(12) United States Patent
Douglas et al.

(10) Patent No.: US 7,520,895 B2
(45) Date of Patent: Apr. 21, 2009

(54) SELF EXPANDING BIFURCATED ENDOVASCULAR PROSTHESIS

(75) Inventors: Myles S. Douglas, Phoenix, AZ (US); Gilbert Madrid, Laguna Niguel, CA (US); Mehrdad M. Shokoohi, Rancho Palos Verdes, CA (US)

(73) Assignee: Endologix, Inc., Irvine, CA (US)

( * ) Notice: Subject to any disclaimer, the term of this patent is extended or adjusted under 35 U.S.C. 154(b) by 321 days.

(21) Appl. No.: 10/119,525

(22) Filed: Apr. 8, 2002

(65) Prior Publication Data

US 2002/0165602 A1 Nov. 7, 2002

(51) Int. Cl.
*A61F 2/06* (2006.01)
(52) U.S. Cl. ..................................... 623/1.35
(58) Field of Classification Search ......... 606/191–198; 623/1.11, 1.35, 1.15
See application file for complete search history.

(56) References Cited

U.S. PATENT DOCUMENTS

| | | |
|---|---|---|
| 2,127,903 A | 8/1938 | Bowen |
| 2,845,959 A | 8/1958 | Sidebotham |
| 2,990,605 A | 7/1961 | Dernsyk |
| 3,029,819 A | 4/1962 | Starks |
| 3,096,560 A | 7/1963 | Liebig |
| 3,805,301 A | 4/1974 | Liebig |
| 4,497,074 A | 2/1985 | Rey et al. |
| 4,501,263 A | 2/1985 | Harbuck |
| 4,503,568 A | 3/1985 | Madras |
| 4,592,754 A | 6/1986 | Gupte et al. |
| 4,617,932 A | 10/1986 | Kornberg |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,994,071 A | 2/1991 | MacGregor |
| 5,019,090 A | 5/1991 | Pinchuk |
| 5,035,706 A | 7/1991 | Giantureo et al. |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,133,732 A | 7/1992 | Wiktor |
| 5,135,536 A | 8/1992 | Hillstead |
| 5,156,619 A | 10/1992 | Ehrenfeld |
| 5,178,634 A | 1/1993 | Martinez |
| 5,197,976 A | 3/1993 | Herweck et al. |

(Continued)

FOREIGN PATENT DOCUMENTS

CA 2007648 4/1991

(Continued)

OTHER PUBLICATIONS

US 6,413,270, 07/2002, Thornton et al. (withdrawn)

*Primary Examiner*—Kevin T. Truong
(74) *Attorney, Agent, or Firm*—Knobbe Martens Olson & Bear LLP

(57) ABSTRACT

Disclosed is a bifurcated tubular endoluminal vascular prosthesis, useful in treating, for example, an abdominal aortic aneurysm. The prosthesis comprises a self expandable wire support structure surrounded at least in part by a flexible tubular membrane. A delivery catheter and methods are also disclosed.

32 Claims, 16 Drawing Sheets

U.S. PATENT DOCUMENTS

| | | | |
|---|---|---|---|
| 5,201,757 A | 4/1993 | Heyn et al. |
| 5,256,141 A | 10/1993 | Gencheff et al. |
| 5,275,622 A | 1/1994 | Lazarus et al. |
| 5,282,824 A | 2/1994 | Gianturco |
| 5,304,200 A | 4/1994 | Spaulding |
| 5,314,472 A | 5/1994 | Fontaine |
| 5,316,023 A | 5/1994 | Palmaz et al. |
| 5,342,387 A | 8/1994 | Summers |
| 5,360,443 A | 11/1994 | Barone et al. |
| 5,366,504 A | 11/1994 | Andersen et al. |
| 5,370,683 A | 12/1994 | Fontaine |
| 5,383,892 A | 1/1995 | Cardon et al. |
| 5,387,235 A | 2/1995 | Chuter |
| 5,405,377 A | 4/1995 | Cragg |
| 5,415,664 A | 5/1995 | Pinchuk |
| 5,423,886 A | 6/1995 | Arru et al. |
| 5,425,765 A | 6/1995 | Tiefenbrun et al. |
| 5,443,498 A | 8/1995 | Fontaine |
| 5,443,500 A | 8/1995 | Sigwart |
| 5,456,713 A | 10/1995 | Chuter |
| 5,489,295 A | 2/1996 | Piplani et al. |
| 5,496,365 A | 3/1996 | Sgro |
| 5,507,767 A | 4/1996 | Maeda et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,211 A | 8/1996 | An et al. |
| 5,554,181 A | 9/1996 | Das |
| 5,562,728 A | 10/1996 | Lazarus et al. |
| 5,578,072 A | 11/1996 | Barone et al. |
| 5,591,229 A | 1/1997 | Parodi |
| 5,607,445 A | 3/1997 | Summers |
| 5,609,625 A | 3/1997 | Piplani et al. |
| 5,609,627 A | 3/1997 | Goicoechea et al. |
| 5,628,788 A | 5/1997 | Pinchuk |
| 5,632,772 A | 5/1997 | Alcime et al. |
| 5,643,339 A | 7/1997 | Kavteladze et al. |
| 5,647,857 A | 7/1997 | Anderson et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,700 A | 9/1997 | Lazarus |
| 5,662,702 A | 9/1997 | Keranen |
| 5,665,115 A | 9/1997 | Cragg |
| 5,665,117 A | 9/1997 | Rhodes |
| 5,674,241 A | 10/1997 | Bley et al. |
| 5,674,276 A | 10/1997 | Andersen et al. |
| 5,676,696 A | 10/1997 | Marcade |
| 5,676,697 A | 10/1997 | McDonald |
| 5,679,400 A | 10/1997 | Tuch |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,716,365 A | 2/1998 | Goicoechea et al. |
| 5,716,393 A | 2/1998 | Lindenberg et al. |
| 5,718,973 A | 2/1998 | Lewis et al. |
| 5,749,880 A | 5/1998 | Banas et al. |
| 5,755,771 A | 5/1998 | Penn et al. |
| 5,800,456 A | 9/1998 | Maeda et al. |
| 5,824,037 A | 10/1998 | Fogarty et al. |
| 5,851,228 A | 12/1998 | Pinheiro |
| 5,906,640 A | 5/1999 | Penn et al. |
| 5,916,263 A | 6/1999 | Goicoechea et al. |
| 5,919,225 A | 7/1999 | Lau et al. |
| 5,928,279 A | 7/1999 | Shannon et al. |
| 5,948,018 A | 9/1999 | Dereume et al. |
| 5,961,548 A * | 10/1999 | Shmulewitz ............... 623/1.35 |
| 6,017,363 A | 1/2000 | Hojeibane |
| 6,030,414 A * | 2/2000 | Taheri ........................ 623/1.1 |
| 6,039,749 A | 3/2000 | Marin et al. |
| 6,039,755 A | 3/2000 | Edwin et al. |
| 6,039,758 A | 3/2000 | Quiachon et al. |
| 6,051,020 A | 4/2000 | Goicoechea et al. |
| 6,070,589 A | 6/2000 | Keith et al. |
| 6,074,398 A | 6/2000 | Leschinsky |
| 6,077,296 A * | 6/2000 | Shokoohi et al. ........... 623/1.11 |
| 6,077,297 A | 6/2000 | Robinson et al. |
| 6,080,191 A * | 6/2000 | Summers ................... 623/1.22 |
| 6,086,611 A * | 7/2000 | Duffy et al. ................. 623/1.35 |
| 6,106,548 A | 8/2000 | Roubin et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,165,195 A * | 12/2000 | Wilson et al. ............... 606/194 |
| 6,168,610 B1 | 1/2001 | Marin et al. |
| 6,187,037 B1 | 2/2001 | Satz |
| 6,192,944 B1 | 2/2001 | Greenhalgh |
| 6,197,049 B1 | 3/2001 | Shaolian et al. |
| 6,283,991 B1 | 9/2001 | Cox et al. |
| 6,331,190 B1 | 12/2001 | Shokoohi et al. |
| 6,395,019 B2 | 5/2002 | Chobotov |
| 6,508,835 B1 | 1/2003 | Shaolian et al. |
| 6,520,988 B1 * | 2/2003 | Colombo et al. ........... 623/1.35 |
| 6,551,350 B1 | 4/2003 | Thornton et al. |
| 6,733,523 B2 | 5/2004 | Shaolian et al. |
| 2006/0264801 A1 | 11/2006 | Bolling et al. |
| 2006/0271163 A1 | 11/2006 | Shokoohi et al. |
| 2006/0287713 A1 | 12/2006 | Douglas et al. |
| 2007/0112412 A1 | 5/2007 | Shokoohi et al. |

FOREIGN PATENT DOCUMENTS

| | | |
|---|---|---|
| CA | 2127458 A1 | 7/1993 |
| CA | 2 220 141 | 7/1997 |
| CA | 2287406 A3 | 12/1997 |
| EP | 0 177 330 B1 | 6/1991 |
| EP | 0 596 145 A1 | 5/1994 |
| EP | 0 621 015 A1 | 10/1994 |
| EP | 0 659 389 A1 | 6/1995 |
| EP | 0 740 928 A2 | 11/1996 |
| EP | 0 747 020 A2 | 12/1996 |
| EP | 0 775 470 A1 | 5/1997 |
| JP | 04-25755 | 6/1990 |
| JP | 07-47134 | 3/1994 |
| JP | 30-09638 | 4/1994 |
| JP | 08-52165 | 6/1995 |
| JP | 09-164209 | 12/1995 |
| WO | WO 93/13825 | 7/1993 |
| WO | WO 96/38101 | 12/1996 |
| WO | WO 96/39999 | 12/1996 |
| WO | WO 96/41589 | 12/1996 |
| WO | WO 97/10777 | 3/1997 |
| WO | WO 99/44536 | 9/1999 |
| WO | WO 99/47077 | 9/1999 |

* cited by examiner

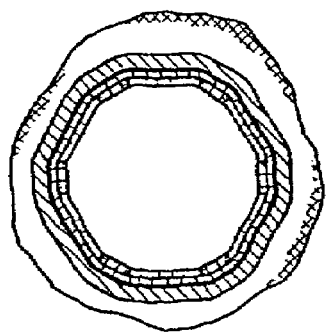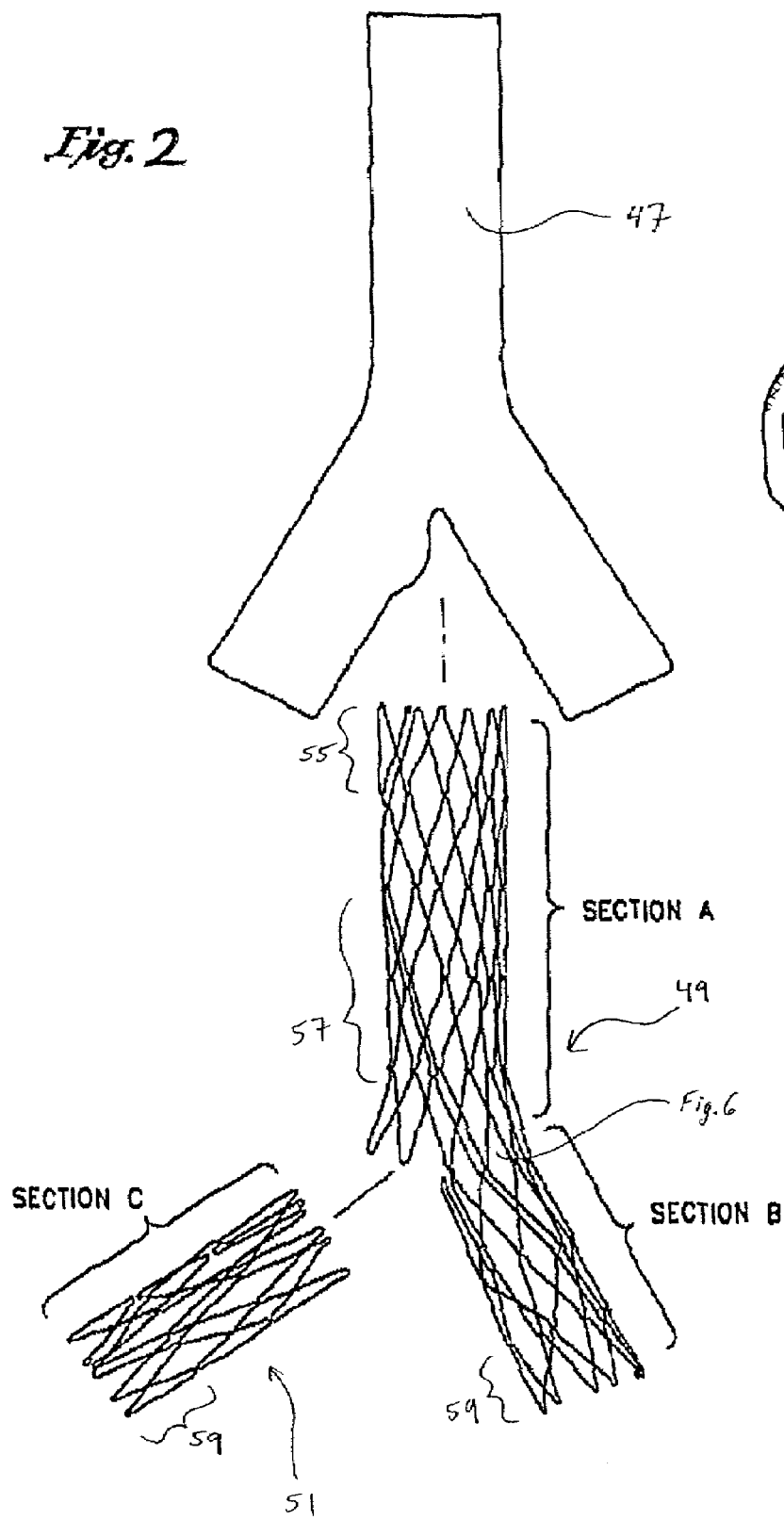

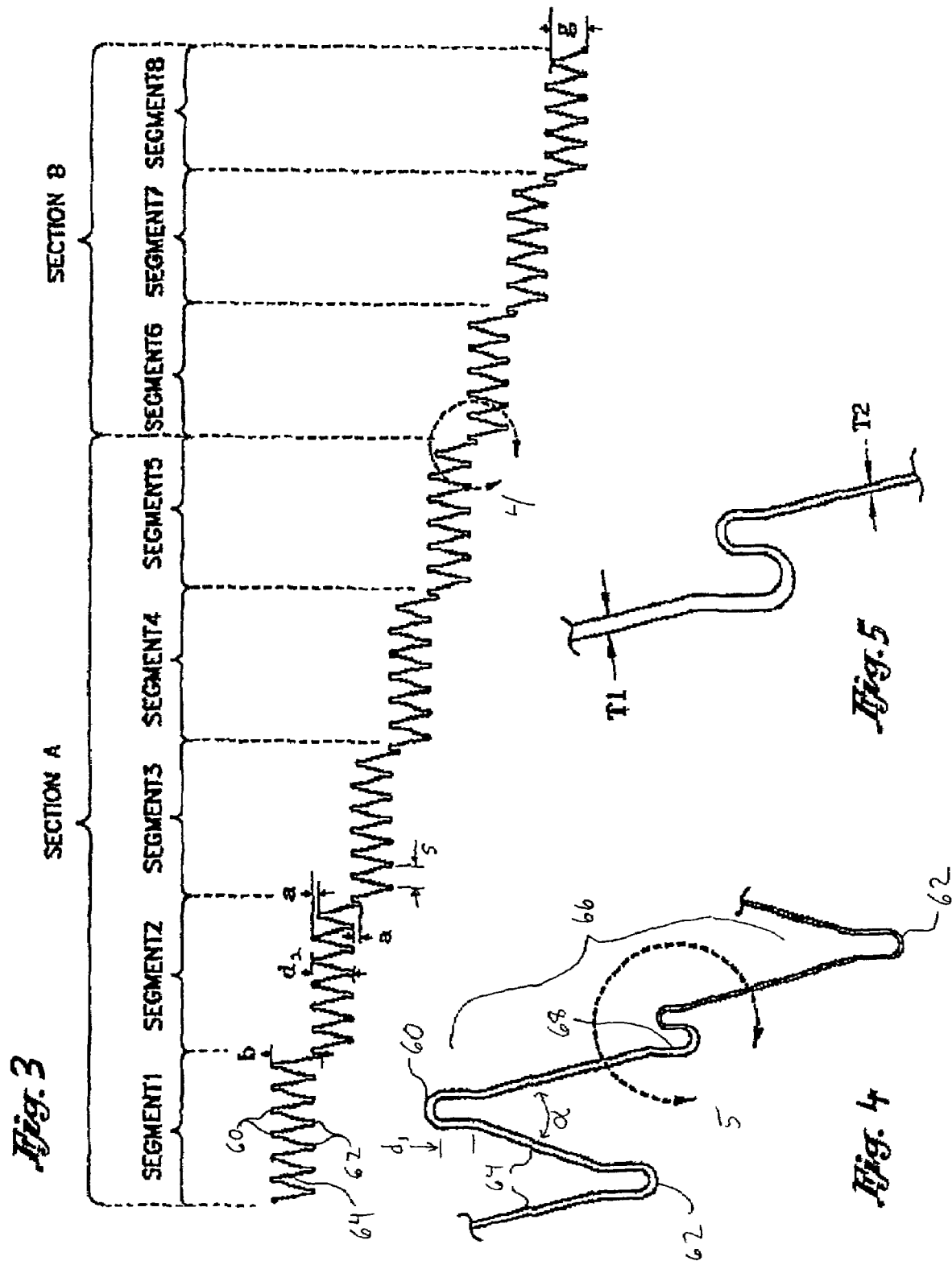

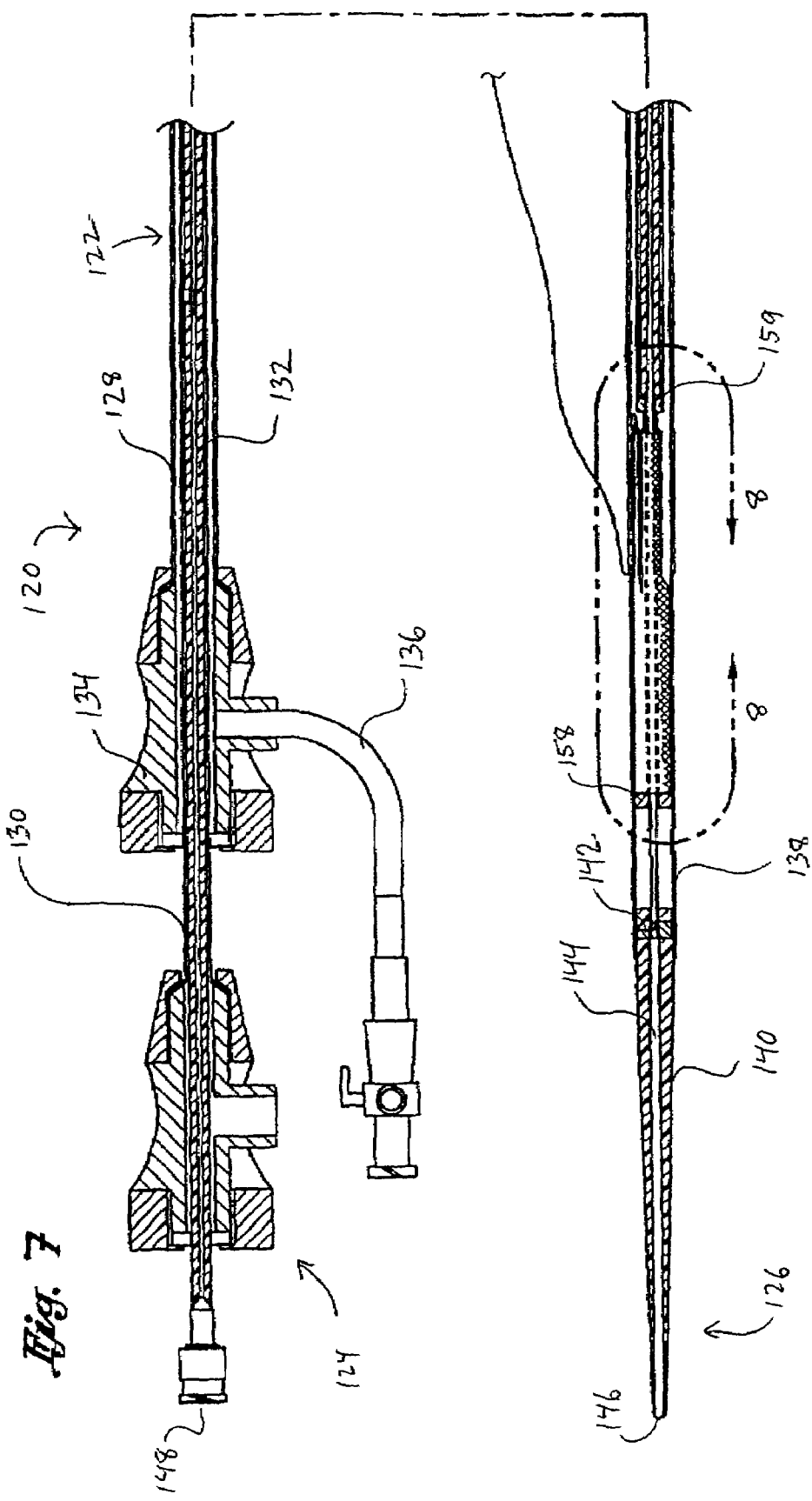

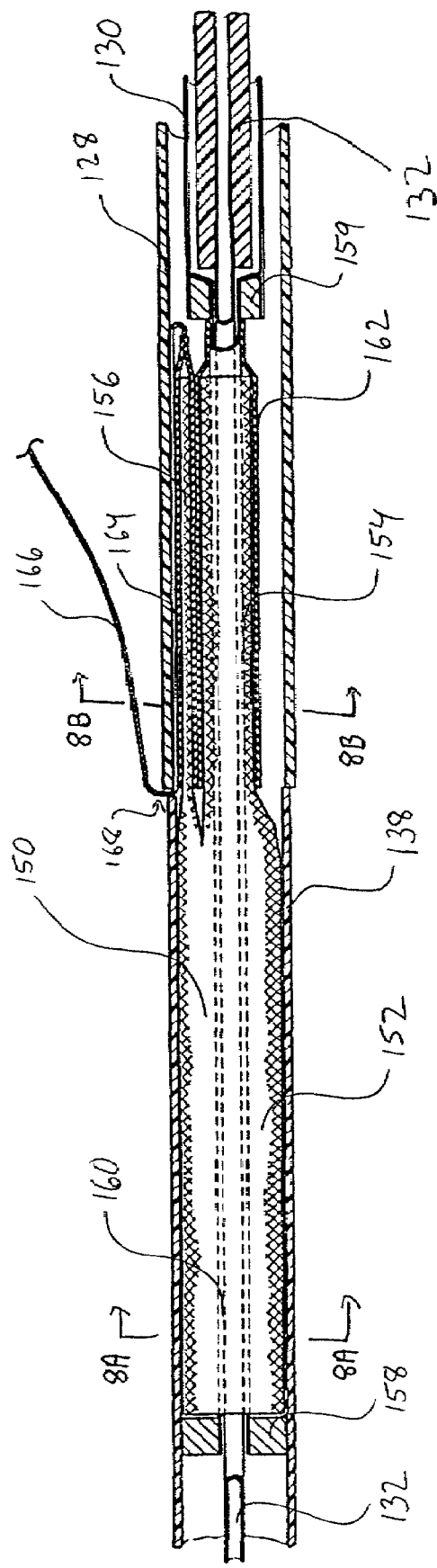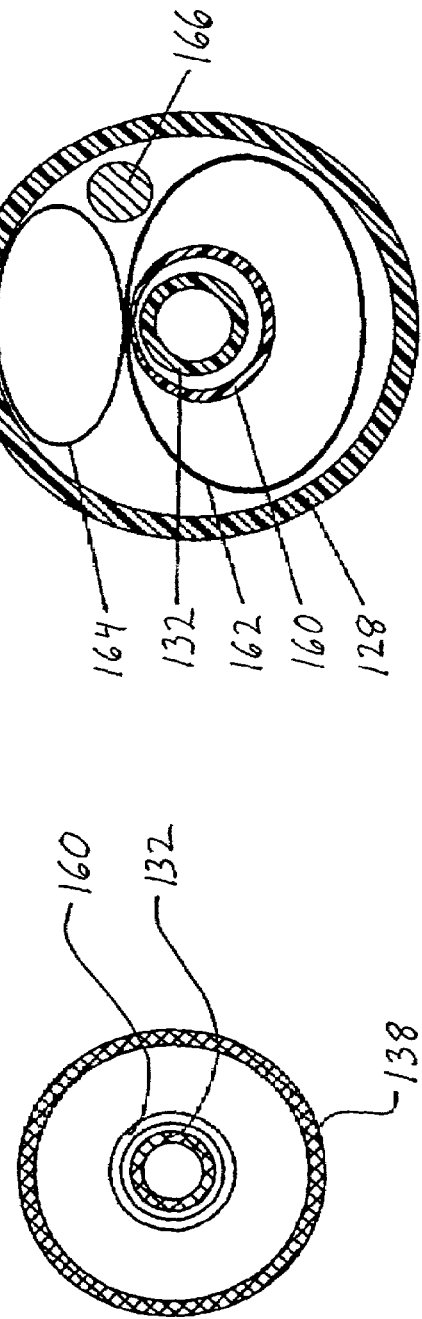

SELF EXPANDING BIFURCATED ENDOVASCULAR PROSTHESIS

BACKGROUND OF THE INVENTION

The present invention relates to endoluminal repair of a vessel, and, in particular, repair of a bifurcation aneurysm such as at the iliac bifurcation of the abdominal aorta.

Endoluminal repair or exclusion of aortic aneurysms has been performed for the past several years. The goal of endoluminal aortic aneurysm exclusion has been to correct this life threatening disease in a minimally invasive manner in order to effectuate a patient's quick and complete recovery. Various vascular grafts exist in the prior art which have been used to exclude aortic aneurysms. These prior art grafts have met varying degrees of success.

Initially, straight tube grafts were used in the infrarenal abdominal aorta to exclude the aneurysmal sac from the blood stream thereby resulting in the weakened aortic wall being protected by the graft material. These straight tube grafts were at first unsupported meaning that they employed stents at their proximal and distal ends to anchor the proximal and distal ends of the graft to the healthy portions of the aorta thereby leaving a midsection of the graft or prosthesis that did not have any internal support. Although this type of graft at first appeared to correct the aortic aneurysm, it met with many failures. The unsupported nature of its midsection allowed the graft to migrate distally as well as exhibit significant proximal leakage due to the enlargement of the aorta without adaptation of the graft, such as enlargement of the graft, to accommodate the change in diameter of the aorta.

Later, technical improvements in stent design led to "self-expanding" stents. In addition, later improvements produced "Nitinol" stents which had a "memory" that was capable of expanding to a predetermined size. Coincidentally, graft designers began to develop bifurcated grafts having limbs which extended into the iliac arteries. The development of bifurcated grafts allowed for the treatment of more complex aneurysms. With the advent of bifurcated grafts, the need for at least a one centimeter neck from the distal aspect of the aneurysmal sac to the iliac bifurcation in order to treat the aneurysm with an endoluminal graft was no longer needed. However, proximal necks of at least 0.5 to 1 centimeter distance from the renal arteries to the most proximal aspect of the aneurysm are still generally required.

Many bifurcated grafts are of a two-piece design. The two-piece designs require the insertion of a contralateral limb through a separate access site. These types of grafts are complex to deploy and have the potential for leakage at the connection site of the two limbs of the graft.

One piece bifurcated grafts are also well known in the art. For example, U.S. Pat. No. 2,845,959 discloses a one piece seamless woven textile bifurcated tube for use as an artificial artery. Yarns of varying materials can be used to weave the bifurcated graft including nylon and plastic yarns. U.S. Pat. Nos. 3,096,560 and 3,029,9819 issued to Liebig and Starks, respectively, disclose woven one piece bifurcated grafts which are constructed by performing specific types of winding and weaving about a smooth bifurcated mandrel.

U.S. Pat. No. 4,497,074 describes a one piece bifurcated graft which is made from a preformed support in the shape of the bifurcated graft. In a first stage, a gel enabling a surface state close to that of the liquid-air interface to be obtained at the gel-air interface is deposited by dipping or coating the preform with a sol which is allowed to cool. A hardenable flexible material such as a silicone elastomer is applied by dipping or spraying the material on the mold in a second stage. Finally, after hardening of the material, the prosthesis is removed from the mold. In U.S. Pat. No. 4,816,028 issued to Kapadia et al., there is shown a one piece woven bifurcated vascular graft having a plurality of warp threads running in the axial direction and a plurality of weft threads running in the transverse direction. Further, U.S. Pat. No. 5,108,424 issued to Hoffman, Jr. et al. discloses a one piece bifurcated collagen-impregnated dacron graft. The bifurcated graft includes a porous synthetic vascular graft substrate formed by knitting or weaving with at least three applications of dispersed collagen fibrils.

The Herweck et al. patent, U.S. Pat. No. 5,197,976, discloses a continuous one piece bifurcated graft having plural longitudinally parallel tube structures which are attached to one another over at least a portion of their longitudinal exteriors. The tube structures can be manually separated to form a branched tubular structure. The prosthesis is manufactured by paste forming and stretching and/or expanding highly crystalline unsintered polytetrafluoroethylene (PTFE). Paste forming includes mixing the PTFE resin with a lubricant, such as mineral spirits, and then forming the resin by extrusion into shaped articles.

Although all of the above-described one piece bifurcated grafts have eliminated the problems of leakage and graft failure at the suture or juncture site associated with two piece bifurcated grafts which join together two separate grafts to form the bifurcated graft, problems still exist with these one piece bifurcated grafts. For example, the previously described one piece bifurcated grafts do not include an integral support structure to prevent the deformation, twisting or collapse of the graft limbs. Further, the same problems with graft migration that existed with straight tube grafts still exist with the one piece bifurcated grafts. Accordingly, there is a need for a stable and durable bifurcated vascular graft which is structured to prevent the migration of the graft and the deformation and obstruction of the blood flow through the limbs of the bifurcated graft.

Endoluminal implantation is a common technique for implanting vascular grafts. Typically, this procedure involves percutaneously inserting a vascular graft or prosthesis by using a delivery catheter. This process eliminates the need for major surgical intervention thereby decreasing the risks associated with vascular and arterial surgery. Various catheter delivery systems for prosthetic devices are described in the prior art.

For example, bifurcated vascular grafts have been created by combining grafts with stents on delivery systems in order to secure the graft ends to the blood vessel thereby stabilizing the bifurcated graft. In U.S. Pat. No. 5,360,443 issued to Barone et al., a method for repairing an abdominal aortic aneurysm is described. The method comprises the steps of (1) connecting an expandable and deformable tubular member, such as a stent, to each of the tubular passageways of a bifurcated graft, (2) disposing the bifurcated graft and deformable tubular members within the aortic and iliac arteries, and (3) expanding and deforming each deformable tubular member with a catheter to secure each tubular passageway of the bifurcated graft within the appropriate artery. This reference only discloses a catheter delivery method for deploying the aortic portion of the bifurcated graft. The same catheter is supposedly used to also expand and secure the associated stents within the iliac arteries.

The Palmaz et al. patent, U.S. Pat. No. 5,316,023, describes a method and apparatus for repairing an abdominal aortic aneurysm in an aorta at the iliac arteries. This method includes the steps of connecting a first tubular graft to a first deformable and expandable tubular member, connecting a second tubular graft to a second deformable and expandable tubular member, disposing the first tubular graft and first tubular member upon a first catheter having an inflatable portion, disposing the second tubular graft and second tubular member upon a second catheter having an inflatable portion, intraluminally delivering the first and second tubular grafts, tubular members and catheters to the aorta and disposing at least a portion of each tubular graft within the abdominal aortic aneurysm, and expanding the tubular members with the inflatable catheters to secure them and at least a portion of their associated tubular grafts within the aorta. This patent reference employs two separate unconnected straight grafts which are employed within an aorta to form a bifurcated graft.

Further, U.S. Pat. No. 4,617,932 issued to Kornberg discloses a device for inserting a graft into an artery comprising a plurality of nested tubes each having an upper and lower end. A first outer tube has a means for guiding and positioning an arm means at its upper end. The arm means is movably attached to the upper end of another tube located inside of the first tube and extending above the first outer tube. The lower ends of the tubes are adaptable for fastening means and the inside tube extends below the end of the first outer tube. Delivery and placement of a bifurcated graft is illustrated. U.S. Pat. No. 5,522,883 issued to Slater et al. describes an endoprosthesis stent/graft deployment system which includes a tubular delivery catheter, a radially expandable prosthesis positioned over the catheter, a removable endoprosthesis support assembly located adjacent the catheter opening and having an arm extending through the catheter which keeps the endoprosthesis in a compressed state, and a release mechanism insertable through the catheter for removing the support assembly.

U.S. Pat. No. 5,104,399 issued to Lazarus also describes an artificial graft and delivery method. The delivery system includes a capsule for transporting the graft through the blood vessel, a tube connected to the vessel which extends exterior to the vessel for manipulation by a user, and a balloon catheter positioned within the tube. Finally, U.S. Pat. No. 5,489,295 issued to Piplani et al. discloses a bifurcated graft and a method and apparatus for deploying the bifurcated graft. The Piplani et al. graft includes a main tubular body, first and second tubular legs joined to the main tubular body in a bifurcation, a first expandable attachment means for anchoring the main body located adjacent the opening for the first body, and a second expandably attachment means located adjacent the opening of the first tubular leg for anchoring the first tubular leg. The graft is intraluminally implanted using a catheter that is inserted into the aortic bifurcation through a first iliac artery so that the first attachment means adjacent the opening of the main body can be anchored in the aorta and the second attachment means adjacent the opening of the first tubular leg can be anchored in the first iliac artery. The second tubular leg is deployed into the second iliac artery by using a pull line attached to the second tubular leg. The Piplani et al. patent also discloses a deployment device consisting of a capsule catheter, a balloon catheter, and a separate expandable spring attachment means.

The previously described deployment methods, systems and devices do not allow for a bifurcated graft which is fully supported with self-expandable stents to be delivered and implanted within an arterial bifurcation. A use of any of the previously described deployment devices or systems to implant the structural supported bifurcated graft of the present invention would result in failure due to the inability of those devices and systems to deliver and anchor the second supported limb within the second iliac artery. The previously described methods and systems simply do not allow for the delivery and implantation of a bifurcated vascular graft whose three open ends are supported by stents. Accordingly, not only is there a need for a structurally supported stable and durable bifurcated graft which is not susceptible to migration and leaking, but there is also a need for a delivery apparatus and method for deploying and implanting such a bifurcated graft.

SUMMARY OF THE INVENTION

There is disclosed in accordance with one aspect of the present invention, a bifurcated endoluminal prosthesis. The prosthesis comprises a proximal wire support section having a proximal end, a distal end, and a central lumen extending therethrough. A first wire branch section is provided at the distal end of the proximal support, and a second wire branch section is also provided at the distal end of the proximal support. At least the proximal support section and the first branch section are formed from a single length of wire.

Preferably, the proximal support comprises at least two axially adjacent tubular segments, joined by a connector therebetween. The wire in each segment is formed into a series of proximal bends and a series of distal bends, creating a series of struts connecting the proximal bends and distal bends to form a tubular segment wall. Preferably, the wire decreases in cross-section from a relatively large cross-section in the proximal wire support section to a relatively small cross-section at the distal end of at least one of the first and second wire branch sections. A tubular sheath, such as PTFE or Teflon, is supported on the wire cage.

In accordance with another aspect of the present invention, there is provided a method of making a bifurcated endoluminal prosthesis. The method comprises the steps of providing a first length of wire, and forming the wire into two or more zig zag sections. Each zig zag section is separated by a crosslink. The formed wire is rolled about an axis to produce a proximal tubular support section and a first distal tubular branch. A second length of wire is formed into a tube, and attached to the distal end of the proximal tubular support section to produce a second distal tubular branch.

Preferably, the method further comprises the step of positioning a tubular polymeric sleeve concentrically on at least a part of the prosthesis.

In accordance with a further aspect of the present invention, there is provided a multi-zone endoluminal bifurcation prosthesis. The prosthesis comprises a tubular wire support having a proximal end, a distal end and a central lumen extending therethrough. The wire support comprises at least a first and a second axially adjacent tubular segments, joined by a connector extending therebetween, wherein the first tubular segment has a different radial strength than the second tubular segment. A first and a second tubular wire branches are connected to the distal end of the support to produce a multi-zone endoluminal bifurcation prosthesis.

In accordance with a further aspect of the present invention, there is provided a method of implanting a self-expandable tubular prosthesis at the junction of a main vessel and first and second branch vessels. The method comprises the steps of advancing a delivery catheter distally through at least a portion of the first branch and into the main vessel, the catheter containing a prosthesis having a main section and first and second branch sections. A main sheath is distally advanced on the catheter to deploy the main section of the prosthesis within the main vessel. A first branch sheath is proximally retracted to deploy the first branch portion of the prosthesis within the first branch vessel. A second branch sheath is proximally retracted to deploy the second branch portion of the prosthesis within the second branch vessel.

Preferably, the proximally retracting a second branch sheath step is accomplished by pulling a wire connected to the second branch sheath, and extending transluminally through the contralateral iliac artery. In one application, the main vessel comprises the aorta, and the first and second branch vessels comprise iliac arteries.

In accordance with a further aspect of the present invention, there is provided a method of deploying first and second iliac branches of a self-expandable prosthesis. The method comprises the steps of positioning the first and second iliac branches of the prosthesis within the first and second iliac arteries, respectively. The positioning step is accomplished while the first and second iliac branches of the prosthesis are constrained by first and second respective retention structures.

The first retention structure is withdrawn from the first branch and transluminally through the first iliac to permit the first branch to expand. The second retention structure is withdrawn from the second branch and transluminally through the second iliac to permit the second branch to expand.

Preferably, the first and second branches of the prosthesis are connected to a main trunk portion for implantation within the aorta. The method additionally comprises the step of advancing a main sheath to deploy the main portion of the prosthesis within the aorta. The order of deploying the first and second branches and main portion of the prosthesis can proceed in any sequence.

In one embodiment of the invention, the withdrawing the first retention structure step comprises withdrawing a tubular sheath from around the first branch. The withdrawing the first retention structure step additionally or alternatively comprises pulling a pull wire transluminally positioned within the iliac.

In accordance with a further aspect of the present invention, there is provided a deployment catheter for deploying a self-expandable graft having a main vessel portion and first and second branch portions. The catheter comprises an elongate flexible body, having a first sheath for containing the main vessel portion of the graft. A second sheath is provided for containing the first branch portion of the graft, and a third sheath is provided for containing the second branch portion of the graft. In one embodiment, the first sheath is axially distally displacable to deploy the main vessel portion of the graft. Preferably, a contra lateral pull wire is attached to the second sheath, for pulling the sheath proximally through the contra lateral iliac to release the first branch portion of the graft.

In accordance with a further aspect of the present invention, there is provided a combination of a deployment catheter and a bifurcation graft, the bifurcation graft having a main portion and first and second branch portions. The combination comprises an elongate flexible body, having proximal and distal ends. The body extends through the main portion and first branch portion of the graft such that the main portion of the graft is disposed distally of the first portion of the graft. A first sheath on the body is provided for containing the first branch portion, and a second sheath is provided for containing the second branch portion.

In one embodiment, a pull wire is provided for pulling the second sheath proximally from the second branch portion. In addition, a main sheath is preferably axially movably positioned on the body for containing the main portion of the graft.

In accordance with a further aspect of the present invention, there is provided a method of deploying a bifurcation graft at a bifurcation site in a vessel. The method comprises the steps of introducing a catheter having the bifurcation graft and at least one removable graft retention structure thereon through a first percutaneous puncture. The graft is deployed at the site, and the catheter is thereafter removed through the first percutaneous puncture. The removable graft retention structure is thereafter removed through a second percutaneous puncture.

Further features and advantages of the present invention will become apparent to those of skill in the art in view of the disclosure herein, when considered together with the attached drawings and claims.

BRIEF DESCRIPTION OF THE DRAWINGS

FIG. 1A is an elevational view of the implanted graft taken along the lines 1a-1a of FIG. 1.

FIG. 2 is an exploded view of the bifurcated vascular prosthesis in accordance with the present invention, showing a two-part self expandable wire support structure separated from an outer tubular sleeve.

FIG. 3 is a plan view of a formed wire useful for rolling about an axis into an aortic trunk segment and an iliac branch segment support structure in accordance with the present invention.

FIG. 4 is an enlarged detail view of a portion of the formed wire illustrated in FIG. 3.

FIG. 5 is a detail view of a portion of the wire illustrated in FIG. 4.

FIG. 7 is a side elevational cross section of a deployment catheter in accordance with the present invention.

FIG. 8 is an enlarged side elevational view of the portion of the catheter of FIG. 7 identified by the lines 8-8.

FIG. 8A is a cross-section taken along the lines 8a-8a in FIG. 8, with the graft omitted for clarity.

FIG. 8B is a cross-section taken along the lines 8b-8b of FIG. 8, with the iliac branches of the graft omitted for clarity.

DETAILED DESCRIPTION OF PREFERRED EMBODIMENTS

Figure 1:
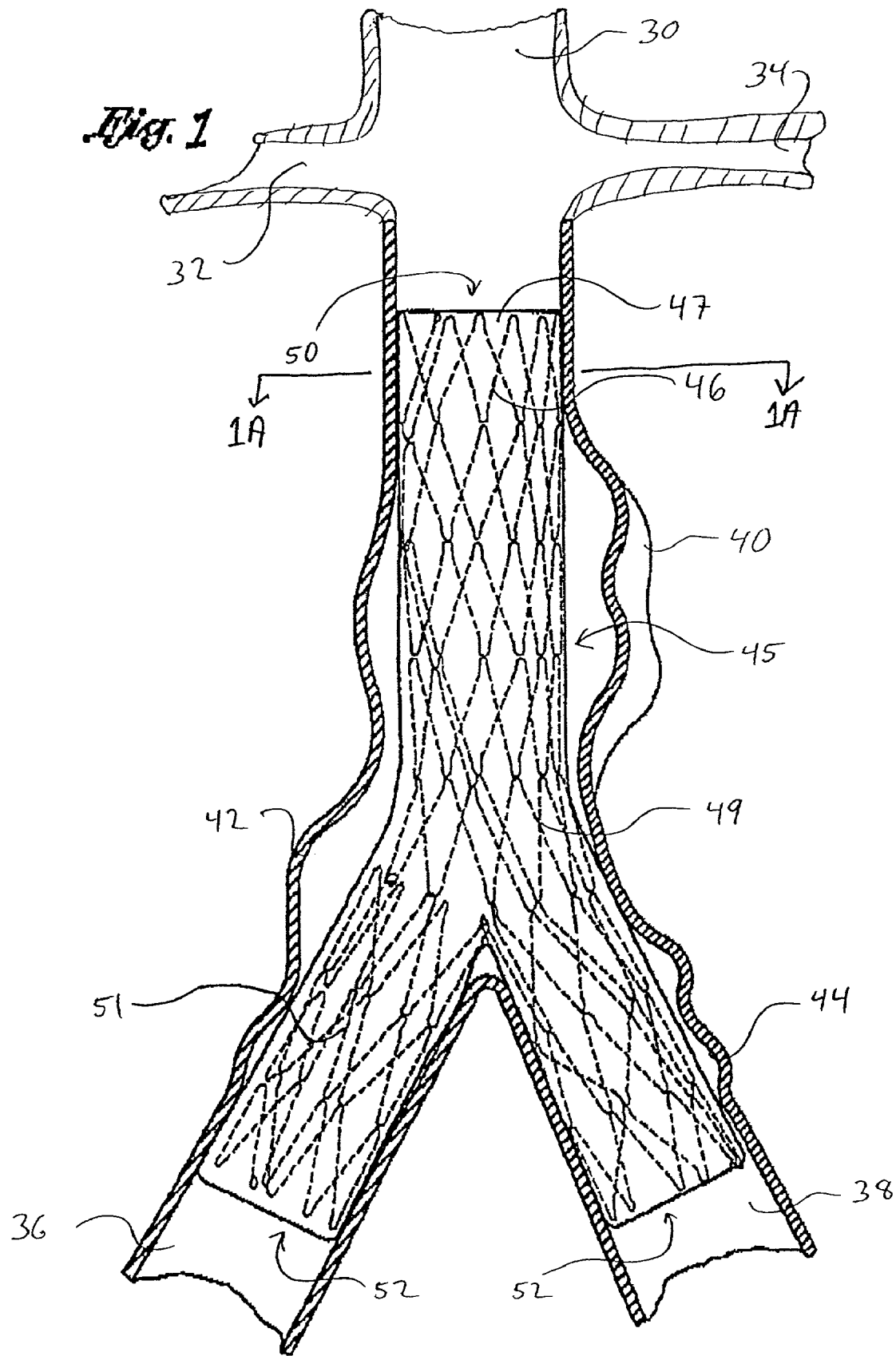
FIG. 1 is a schematic representation of a bifurcated endoluminal vascular prosthesis in accordance with the present invention, positioned at the bifurcation between the abdominal aorta and the right and left common iliac arteries.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification. An abdominal aortic aneurysm 40 is illustrated in the infrarenal portion of the diseased aorta. Portions of the same aneurysm 40 or additional aneurysms extend into a bifurcation region 42 and an iliac region 44 of the left common iliac 38.

An expanded endoluminal vascular prosthesis 45, in accordance with the present invention, is illustrated spanning the aneurysms 40, 42 and 44. The endoluminal vascular prosthesis 45 includes a polymeric sleeve 47 and a tubular wire support 46, which are illustrated in situ in FIG. 1. The sleeve 47 and wire support 46 are more readily visualized in the exploded view shown in FIG. 2. The endoluminal prosthesis 45 illustrated and described herein depicts an embodiment in which the polymeric sleeve 47 is situated concentrically outside of the tubular wire support 46. However, other embodiments may include a sleeve situated instead concentrically inside the wire support or on both of the inside and the outside of the wire support. Alternatively, the wire support may be embedded within a polymeric matrix which makes up the sleeve. Regardless of whether the sleeve 47 is inside or outside the wire support 46, the sleeve may be attached to the wire support by any of a variety of means, including laser bonding, adhesives, clips, sutures, dipping or spraying or others, depending upon the composition of the sleeve 47 and overall graft design.

The polymeric sleeve 47 may be formed from any of a variety of synthetic polymeric materials, or combinations thereof, including PTFE, PE, PET, Urethane, Dacron, nylon, polyester or woven textiles. Preferably, the sleeve material exhibits relatively low inherent elasticity, or low elasticity out to the intended enlarged diameter of the wire cage 46. The sleeve material preferably has a thin profile, such as no larger than about 0.002 inches to about 0.005 inches.

In a preferred embodiment of the invention, the material of sleeve 47 is sufficiently porous to permit ingrowth of endothelial cells, thereby providing more secure anchorage of the prosthesis and potentially reducing flow resistance, shear forces, and leakage of blood around the prosthesis. Porosity in polymeric sleeve materials may be estimated by measuring water permeability as a function of hydrostatic pressure, which will preferably range from about 3 to 6 psi.

The porosity characteristics of the polymeric sleeve 47 may be either homogeneous throughout the axial length of the prosthesis 45, or may vary according to the axial position along the prosthesis 45. For example, referring to FIGS. 1 and 2, different physical properties will be called upon at different axial positions along the prosthesis 45 in use. At least a proximal portion 55 and right and left distal portions 59 of the prosthesis 45 will seat against the native vessel wall, proximally and distally of the aneurysm. In at least these proximal and distal portions, the prosthesis preferably encourages endothelial growth, or, at least, permits endothelial growth to infiltrate portions of the prosthesis in order to enhance anchoring and minimize leakage. A central portion of the prosthesis spans the aneurysm, and anchoring is less of an issue. Instead, minimizing blood flow through the prosthesis wall becomes a primary objective. Thus, in a central zone of the prosthesis 42, the polymeric sleeve 44 may either be nonporous, or provided with pores which minimize or prevent leakage.

A multi-zoned prosthesis 45 may also be provided in accordance with the present invention by positioning a tubular sleeve 47 on a central portion of the prosthesis, such that it spans the aneurysm to be treated, but leaving a proximal attachment zone 55 and distal attachment zones 59 of the prosthesis 45 having exposed wires from the wire support 46. In this embodiment, the exposed wires 46 are positioned in contact with the vessel wall both proximally and distally of the aneurysm, such that the wire, over time, becomes embedded in cell growth on the interior surface of the vessel wall.

In one embodiment of the prosthesis 45, the sleeve 47 and/or the wire support 46 is stepped or tapered, having a relatively larger expanded diameter at the proximal end 50 compared to the distal ends 52. The tapered design may allow the prosthesis to conform better to the natural decreasing distal cross section of the aorta and iliacs to reduce the risk of leakage and graft migration and potentially create better flow dynamics.

The tubular wire support 46 comprises a primary component 49 for traversing the aorta and a first iliac, and a branch component 51 for extending into the second iliac. The primary component 49 is preferably formed from a continuous single length of wire, throughout both the aorta trunk portion and the iliac branch portion. See FIGS. 2 and 3. The wire support 46 is preferably formed in a plurality of discrete segments, connected together and oriented about a common axis. In FIG. 3, Section A corresponds to the aorta trunk portion of the primary component 49, and includes segments 1-5. Segments 6-8 (Section B) correspond to the iliac branch portion of the primary component 49.

Each pair of adjacent segments is connected by a connector 66 as will be discussed. The connectors 66 collectively produce a generally axially extending backbone which adds axial strength to the prosthesis 45. Adjacent segments can be connected both by the backbone, as well as by other structures, including circumferentially extending sutures, solder joints, wire loops and any of a variety of interlocking relationships. The suture can be made from any of a variety of biocompatible polymeric materials or alloys, such as nylon, polypropylene, or stainless steel.

The segmented configuration of the tubular wire support 46 facilitates a great deal of flexibility. Each segment, though joined to adjacent segments, may be independently engineered to yield desired parameters. Each segment may range in axial length from about 0.3 to about 5 cm. Generally, the shorter their length the greater the radial strength. The primary component 49 of an endoluminal prosthesis may include from about 2 to about 50 segments, preferably from about 8 to about 16 segments.

In general, each of the components of the tubular wire support 46 can be varied considerably in diameter, length, and expansion coefficient, depending upon the intended application. For implantation within a typical adult, the aorta trunk portion (section A) of primary component 49 will have a length within the range of from about 5 cm to about 12 cm, and, typically within the range of from about 9 cm to about 10 cm. The unconstrained outside expanded diameter of the section A portion of the primary component 49 will typically be within the range of from about 20 mm to about 40 mm. The unconstrained expanded outside diameter of the section A portion of primary component 49 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 49 and section C will typically be bilaterally symmetrical. Section C length will generally be within the range of from about 1 cm to about 5 cm, and section C diameter will typically be within the range of from about 10 mm to about 20 mm.

In addition to the flexibility and other functional benefits available through employment of different length segments, further flexibility can be achieved through adjustments in the number, angle, or configuration of the wire bends associated with the tubular support.

For example, referring to FIG. 2, the wire cage 46 is dividable into a proximal zone 55, a central zone 57 and a distal zone 59. As has been discussed, the wire cage 46 can be configured to taper from a relatively larger diameter in the proximal zone 55 to a relatively smaller diameter in the distal zone 59. In addition, the wire cage 46 can have a transitional tapered and or stepped diameter within a given zone.

The cage 46 can also be provided with a proximal zone 55 and distal zone 59 that have a larger relative unconstrained expanded diameter than the adjacent portions of central zone 57. This configuration may desirably resist migration of the prosthesis within the vessel. The proximal zone 55 and/or distal zone 59 can be left without an outer covering 47, with the outer sleeve 47 covering only a sufficient portion of the central zone 57 to span the aneurysm. This permits the proximal and distal zones 55, 59 to be in direct contact with tissue proximally and distal to the lesion, which may facilitate endothelial cell growth.

In addition to having differing expanded diameters in different zones of the prosthesis 45, different zones can be provided with a different radial expansion force, such as ranging from about 2 lbs to about 8 lbs. In one embodiment, the proximal zone 55 is provided with a greater radial force than the central zone 57 and/or distal zone 59. The greater radial force can be provided in any of a variety of manners discussed elsewhere herein, such as through the use of an additional one or two or three or more proximal bends 60, distal bends 62 and wall sections 64 compared to a central zone reference segment such as segment 4 or 5 in Section A (FIG. 3). Alternatively, additional spring force can be achieved in the proximal zone 55 through the use of the same number of proximal bends 60 as in the rest of the prosthesis, but with a heavier gauge wire. Radial force in the end zones beyond the expanded diameter limit of the central zone 57 can be achieved by tightening a circumferential suture such that the central zone 57 is retained under compression even in the expanded configuration. By omitting a circumferential suture at the proximal end and/or distal end of the prosthesis, the proximal end and distal end will flair radially outwardly to a fully expanded configuration.

The wire may be made from any of a variety of different alloys, such as elgiloy, nitinol or MP35N, or other alloys which include nickel, titanium, tantalum, or stainless steel, high Co—Cr alloys or other temperature sensitive materials. For example, an alloy comprising Ni 15%, Co 40%, Cr 20%, Mo 7% and balance Fe may be used. The tensile strength of suitable wire is generally above about 300 K psi and often between about 300 and about 340 K psi for many embodiments. In one embodiment, a Chromium-Nickel-Molybdenum alloy such as that marketed under the name Conichrom (Fort Wayne Metals, Indiana) has a tensile strength ranging from 300 to 320 K psi, elongation of 3.5-4.0% and breaking load at approximately 80 lbs to 70 lbs. The wire may be treated with a plasma coating and be provided with or without additional coatings such as PTFE, Teflon, Perlyne, drugs, and others as will be understood by those of skill in the art.

In addition to segment length and bend configuration, discussed above, another determinant of radial strength is wire gauge. The radial strength, measured at 50% of the collapsed profile, preferably ranges from about 2 lb to 8 lb, and generally from about 4 lb to about 5 lb. or more. Preferred wire diameters in accordance with the present invention range from about 0.004 inches to about 0.020 inches. More preferably, the wire diameters range from about 0.006 inches to about 0.018 inches. In general, the greater the wire diameter, the greater the radial strength for a given wire layout. Thus, the wire gauge can be varied depending upon the application of the finished graft, in combination with/or separate from variation in other design parameters (such as the number of struts, or proximal bends 60 and distal bends 62 per segment), as will be discussed.

In one embodiment of the bifurcation graft, the wire gauge remains substantially constant throughout section A of the primary component 49 and steps down to a second, smaller cross section throughout section B of primary component 49. See, for example, FIG. 4.

A wire diameter of approximately 0.018 inches may be useful in the aorta trunk portion of a graft having four segments each having 2.5 cm length per segment, each segment having six struts intended for use in the aorta, while a smaller diameter such as 0.006 inches might be useful for segments of the graft having 5 struts per segment intended for the iliac artery.

In one embodiment of the present invention, the wire diameter is tapered throughout from the proximal to distal ends of the section A and/or section B portions of the primary component 49. Alternatively, the wire diameter may be tapered incremental or stepped down, or stepped up, depending on the radial strength requirements of each particular clinical application. In one embodiment, intended for the abdominal aortic artery, the wire has a cross section of about 0.018 inches in the proximal zone 55 and the wire tapers down regularly or in one or more steps to a diameter of about 0.006 inches in the distal zone 59 of the graft 45. End point dimensions and rates of taper can be varied widely, within the spirit of the present invention, depending upon the desired clinical performance.

In general, in the tapered or stepped wire embodiments, the diameter of the wire in the iliac branches is no more than about 80%, preferably no more than about 50%, and optimally no more than about 35% of the diameter of the wire in the aortic trunk. This permits increased flexibility of the graft in the region of the iliac branches, which has been determined by the present inventors to be clinically desirable.

Referring to FIG. 3, there is illustrated a plan view of the single formed wire used for rolling about a longitudinal axis to produce a primary segment 49 having a five segment aorta section and a three segment iliac section. The formed wire exhibits distinct segments, each corresponding to an individual tubular segment in the tubular support. Additional details of the wire cage layout and construction can be found in copending U.S. patent application Ser. No. 09/034,689 entitled Endoluminal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig zag configuration when the segment is radially expanded. Each segment is connected to the adjacent segment through a connector 66, except at the terminal ends of the graft. The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

Referring to FIG. 4, there is shown an enlarged view of the wire support illustrating a connector 66 portion between adjacent segments 54. In the embodiment shown in FIG. 4, a proximal bend 60 comprises about a 180 degree arc, having a radial diameter ranging from about 0.009 to about 0.070 inches, depending on wire diameter followed on either side of the bend by relatively short lengths of parallel wire spanning an axial distance of d1. The parallel wires thereafter diverge outwardly from one another and form the strut sections 64, or the proximal half of a connector 66. At the distal end of the strut sections 64, the wire forms a distal bend 62, preferably having identical characteristics as the proximal bend 60, except being concave in the opposite direction. The axial direction component of the distance between the apices of the corresponding proximal and distal bends 60, 62 is referred to as ($d_2$) and represents the axial length of that segment. The total expanded angle defined by the bend 60 and the divergent strut sections 64 is represented by $\alpha$. Upon compression to a collapsed state, such as when the graft is within the deployment catheter, the angle $\alpha$ is reduced to $\alpha'$ in which adjacent strut sections 64 are parallel or near parallel to each other. In the expanded configuration, $\alpha$ is generally within the range of from about 30° to about 45° for a segment having about 6 proximal bends 60. The expanded circumferential distance between any two adjacent distal bends 62 (or proximal bends 60) is defined as (s).

In general, the diameter of each proximal bend 60 or distal bend 62 is within the range of from about 0.009 inches to about 0.070 inches depending upon the wire diameter. Bend diameter is preferably as small as possible for a given wire diameter and wire characteristics. As will be appreciated by those of skill in the art, as the diameter is reduced to approach two times the cross section of the wire, the bend 60 or 62 will exceed the elastic limit of the wire, and radial strength of the finished segment will be lost. Determination of a minimum value for the bend diameter, in the context of a particular wire diameter and wire material, can be readily determined through routine experimentation by those of skill in the art. Similarly, although at least some distance of d1 is desired, from the apex to the first bend in the wall section 64, the distance d1 is preferably minimized within the desired radial strength performance requirements. As d1 increases, it may disadvantageously increase the collapsed (implantation) profile of the graft.

As will be appreciated from FIGS. 3 and 4, the sum of the distances (s) in a plane transverse to the longitudinal axis of the finished graft will correspond to the circumference of the finished graft in that plane. For a given circumference, the number of proximal bends 60 or distal bends 62 is thus directly related to the distance (s) in the corresponding plane. Preferably, the finished graft in any single transverse plane will have from about 3 to about 10 (s) dimensions, preferably from about 4 to about 8 (s) dimensions and, more preferably, about 5 or 6 (s) dimensions for an aortic application. Each (s) dimension corresponds to the distance between any two adjacent bends 60-60 or 62-62 as will be apparent from the discussion herein. Each segment can thus be visualized as a series of triangles extending circumferentially around the axis of the graft, defined by a proximal bend 60 and two distal bends 62 or the reverse.

One consequence of the foregoing structure is illustrated in FIG. 1A. A cross-section through the implanted graft shows that the graft will tend to assume more of a polygon than a circular configuration. The number of faces on the polygon is related to the number of proximal bends 60 in each segment. This configuration advantageously increases the radial pressure at localized points around the circumference of the graft, which appears to resist axial migration of the expanded graft within the vessel.

By modifying wire support parameters (such as $d_1$, $d_2$, s, and alpha), the manufacturer enjoys tremendous design control with respect to the total axial length, axial and radial flexibility, radial force and expansion ratios, and consequently prosthesis performance. For example, an increase in the diameter of the bend 60 or 62 translates directly into an increased collapsed profile since the circumference of the collapsed profile can be no smaller than the sum of the bend diameters in a given transverse plane. Similarly, an increase in the number of proximal bends 60 in a given segment may increase radial strength, but will similarly increase the collapsed profile. Since the primary radial force comes from the proximal bends 60 and distal bends 62, the wall sections 64 act as a lever arm for translating that force into radial strength. As a consequence, decreasing the length of strut sections 64 for a given number of proximal bends 60 will increase the radial strength of the segment but call for additional segments to maintain overall graft length. Where a minimal entry profile is desired, radial strength is best accomplished by decreasing the length of wall sections 64 rather than increasing the number of proximal bends 60. On the other hand, increasing the number of (shorter) segments in a given overall length graft will increase the degree of axial shortening upon radial expansion of the graft. Thus, in an embodiment where axial shortening is to be avoided, increased radial strength may be optimized through selection of wire material or wire gauge and other parameters, while minimizing the number of total segments in the graft. Other geometry consequences of the present invention will be apparent to those of skill in the art in view of the disclosure herein.

In one embodiment of the type illustrated in FIGS. 2 and 3, the bend diameter is about 2.0 mm±1 mm for a 0.018 inch wire diameter; $d_1$ is about 3 mm±1 mm; $d_2$ is about 20 mm±1 mm; $d_2$+a (b) is about 23 mm±1 mm; g is about 17 mm, ±1 mm; and a is about 3 mm±1 mm. Specific dimensions for all of the foregoing variables can be varied considerably, depending upon the desired wire configuration, in view of the disclosure herein.

Figure 6:
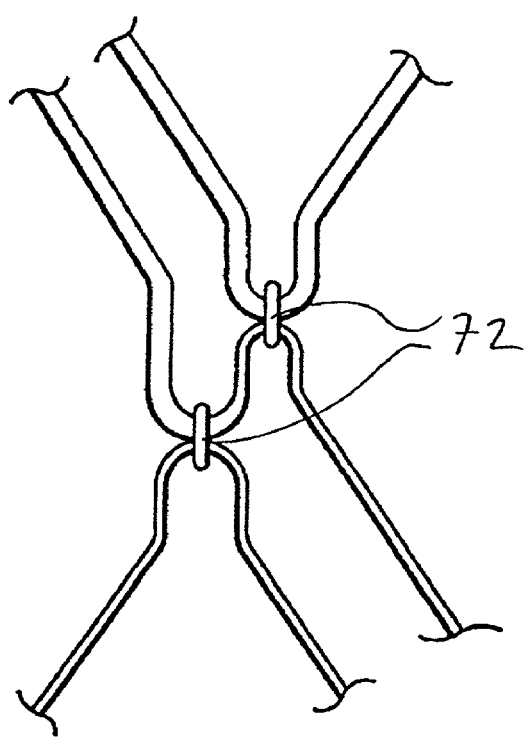
FIG. 6 is an enlarged detail view of the region marked 6-6 in FIG. 2.

Each pair of adjacent segments may be joined by crosslinking of the corresponding proximal and distal bends. See, for example, FIG. 6. Thus, a proximal bend 60 from a distal adjacent segment is connected to the corresponding distal bend 62 of a proximal adjacent segment thereby coupling the proximal and distal segment. The connection between corresponding proximal bends 60 and distal bends 62 can be accomplished in any of a variety of ways as will be apparent to those of skill in the art in view of the disclosure herein. For example, the connection may be accomplished through the use of a link. The link may be a loop of metal such as stainless steel, a suture, a welded joint or other type of connection. Preferably, the link comprises a metal loop or ring which permits pivotable movement of a proximal segment with respect to the adjacent distal segment.

In one example of an endoluminal vascular prosthesis in accordance with the present invention, a link may be provided at each pair of corresponding bends 60, 62, such that six links 72 exist in a plane transverse to the longitudinal axis of the graft at the interface between the proximal segment and the distal segment in a graft having six bends 60, 62 in adjoining planes. Alternatively, links can be provided at less than all of the corresponding bends, such as at every other bend, every third bend, or only on opposing sides of the graft. The distribution of the links 72 in any given embodiment can be selected to optimize the desired flexibility characteristics and other performance criteria in a given design.

Preferably, each link 72 provides a pivotable linkage, such as is accomplished using a metal loop or a suture for link 72. The use of moveable links 72 in combination with the multi-segment structure of the present invention has been determined to optimize patency of the central lumen through the graft throughout a wide variety of angular relationships of the iliac branches to the main trunk, as well as to accommodate nonlinear configurations of the aorta and iliacs. In general, the abdominal aortic anatomy varies considerably from patient to patient, requiring the implanted graft to assume any of a wide variety of different angular orientations. In addition, the path of the aorta as well as the angle of the iliacs is susceptible to change over time following implantation of the graft. The multisegment construction of the present invention enables the graft to change with the surrounding anatomy, while maintaining maximum patency throughout.

The segmented, linked graft of the present invention is also able to be formed into a nonlinear configuration, and retain its form without compromising patency of the central lumen. Thus, the cage construction of the present invention permits both improved anatomical conformance with a wide variety of different abdominal aortic anatomies at the time of implantation as well as improved conformance to the anatomy following post implantation changes which are known to occur. The graft of the present invention thus minimizes late leakage which can otherwise occur due to a poor conformance between the graft and the changing aortic and iliac configurations.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 2, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links as has been discussed previously, through soldering or other attachment means. The attachment means will be influenced by the desirable flexibility of the graft at the bifurcation, which will in turn be influenced by the method of deployment of the vascular graft as will be apparent to those of skill in the art in view of the disclosure herein.

The collapsed prosthesis in accordance with the present invention has a diameter in the range of about 2 to about 10 mm. Preferably, the maximum diameter of the collapsed prosthesis is in the range of about 3 to 6 mm (12 to 18 French). More particularly, the delivery catheter including the prosthesis will be 19 F, 16 F, 14 F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

The self expandable bifurcation graft of the present invention can be deployed at a treatment site in accordance with any of a variety of techniques as will be apparent to those of skill in the art. One such technique is disclosed in copending patent application Ser. No. 08/802,478 entitled Bifurcated Vascular Graft and Method and Apparatus for Deploying Same, filed Feb. 20, 1997, the disclosure of which is incorporated in its entirety herein by reference.

A partial cross sectional side elevational view of one deployment apparatus 120 in accordance with the present invention is shown in FIG. 7. The deployment apparatus 120 comprises an elongate flexible multicomponent tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

Figure 14:
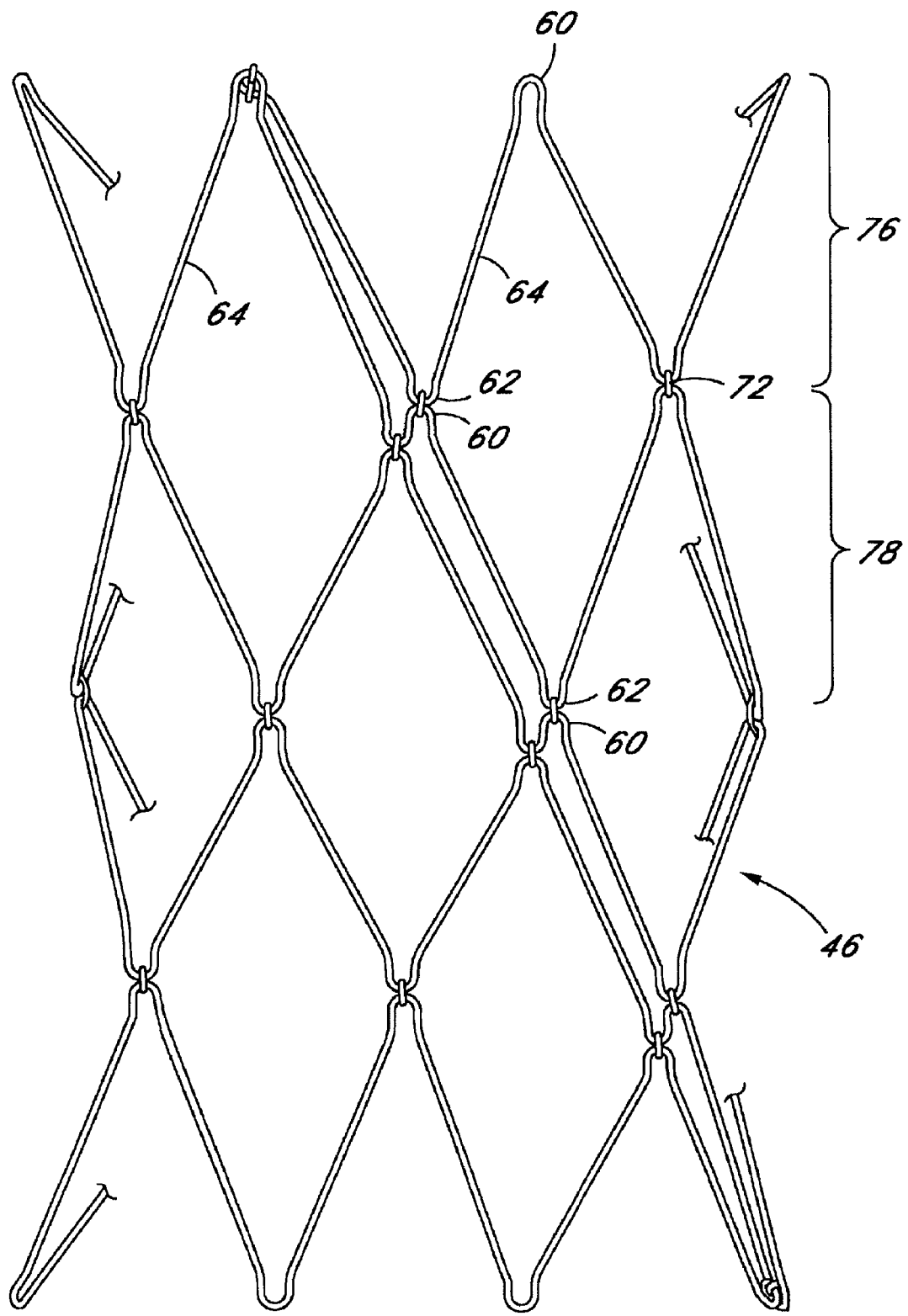
FIG. 14 is an elevational view of a crosslinked wire layout in accordance with the present invention.

For example, in another embodiment of the wire support, illustrated in FIG. 14, each pair of adjacent proximal and distal segments, 76 and 78, may be joined by crosslinking of the corresponding proximal and distal bends. Thus, a proximal bend 60 from a distal segment 78 is connected to the corresponding distal bend 62 of a proximal segment 76, thereby coupling the proximal segment 76 and distal segment 78. The connection between corresponding proximal bends 60 and distal bends 62 can be accomplished in any of a variety of ways as will be apparent to those of skill in the art in view of the disclosure herein. In the illustrated embodiment, the connection is accomplished through the use of a link 72. Link 72 may be a loop of metal such as stainless steel, a suture, a welded joint or other type of connection. Preferably, link 72 comprises a metal loop or ring which permits pivotable movement of a proximal segment 76 with respect to a distal segment 78.

In one example of an endoluminal vascular prosthesis in accordance with the present invention, the proximal segment 76 is provided with six distal bends 62. The corresponding distal segment 78 is provided with six proximal bends 60 such that a one to one correspondence exists. A link 72 may be provided at each pair of corresponding bends 60, 62, such that six links 72 exist in a plane transverse to the longitudinal axis of the graft at the interface between the proximal segment 76 and the distal segment 78. Alternatively, links 72 can be provided at less than all of the corresponding bends, such as at every other bend, every third bend, or only on opposing sides of the graft. The distribution of the links 72 in any given embodiment can be selected to optimize the desired flexibility characteristics and other performance criteria in a given design.

The use of connectors such as cross link 72 enables improved tracking of the graft around curved sections of the vessel. In particular, the wire cage 46 as illustrated in FIG. 14 can be bent around a gentle curve, such that it will both retain the curved configuration and retain patency of the central lumen extending axially therethrough. The embodiment illustrated in FIG. 2 may be more difficult to track curved anatomy while maintaining full patency of the central lumen. The ability to maintain full patency while extending around a curve may be desirable in certain anatomies, such as where the aorta falls to follow the linear infrarenal path illustrated in FIG. 1.

Figure 14A:
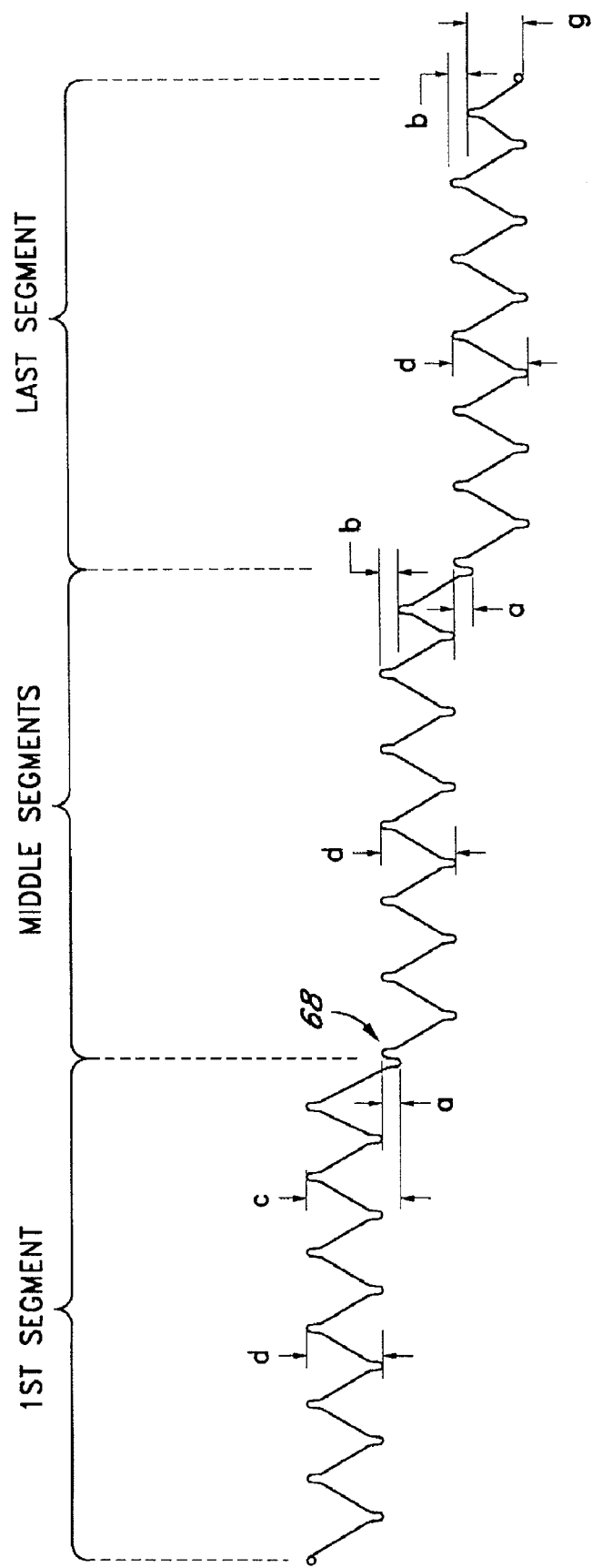
FIG. 14A is a plan view of a formed wire layout useful for forming the crosslinked embodiment of FIG. 8.

Referring to FIG. 14A, there is illustrated a plan view of a formed wire useful for rolling about an axis to produce a multi-segmented support structure of the type illustrated in FIG. 8. In general, the formed wire of FIG. 14A is similar to that illustrated in FIG. 3. However, whereas any given pair of corresponding distal bends 62 and proximal bends 60 of the embodiment of FIG. 3 overlap in the axial direction to facilitate threading a circumferential suture therethrough, the corresponding distal bend 62 and proximal bend 60 of the embodiment illustrated in FIG. 14A may abut end to end against each other or near each other as illustrated in FIG. 14 to receive a connector 72 thereon.

The appropriate axial positioning of a distal bend 62 with respect to a corresponding proximal bend 60 can be accomplished in a variety of ways, most conveniently by appropriate formation of the connector bend 68 between adjacent segments of the wire cage.

Figure 15:
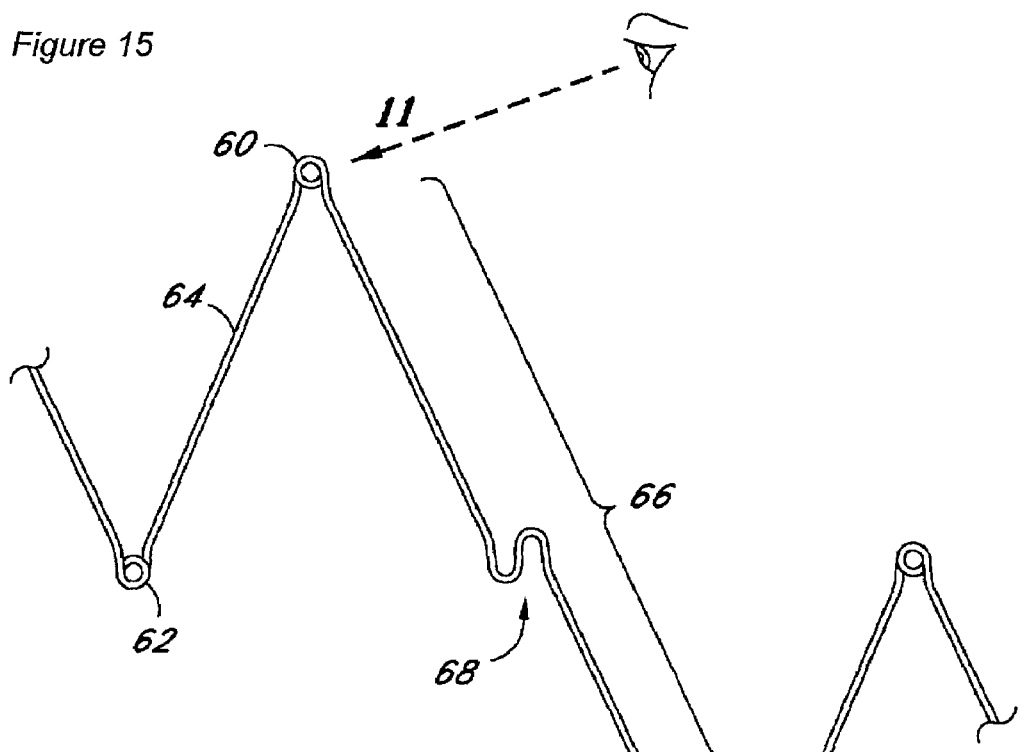
FIG. 15 is a fragmentary view of an alternate wire layout in accordance with a further aspect of the present invention.
Figure 16:
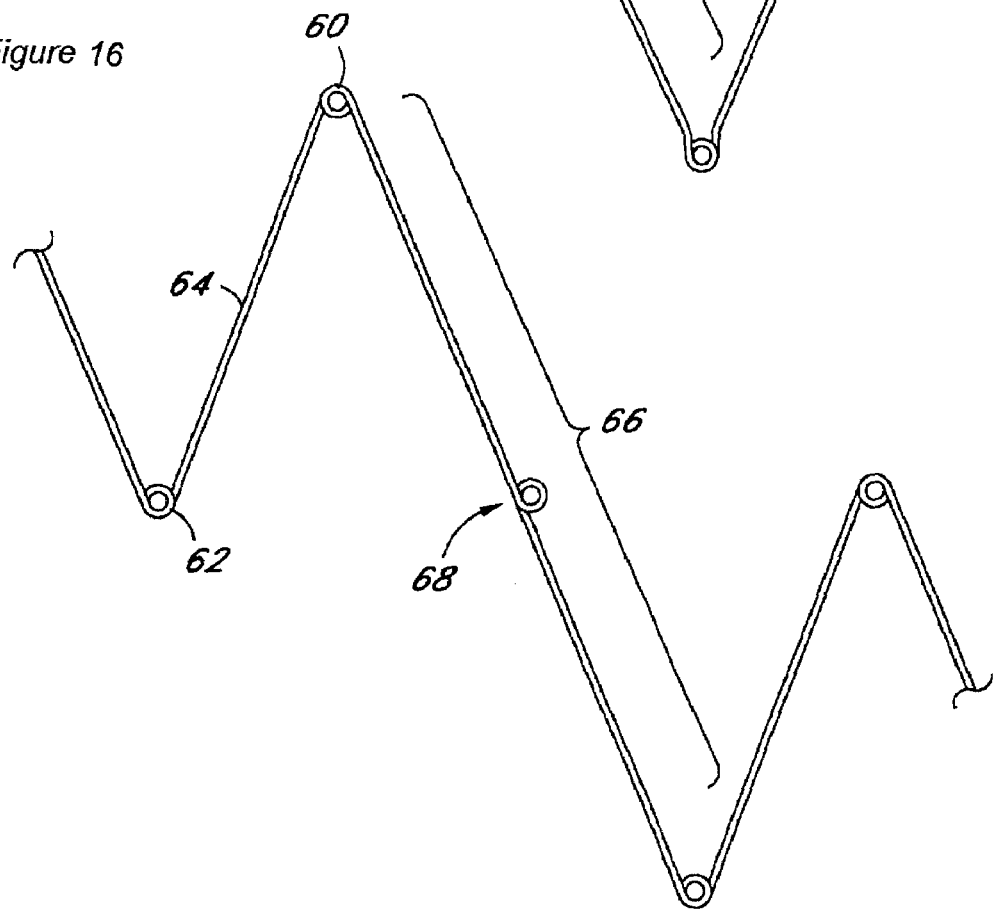
FIG. 16 is a fragmentary view of an alternate wire layout in accordance with a further aspect of the present invention.
Figure 17:
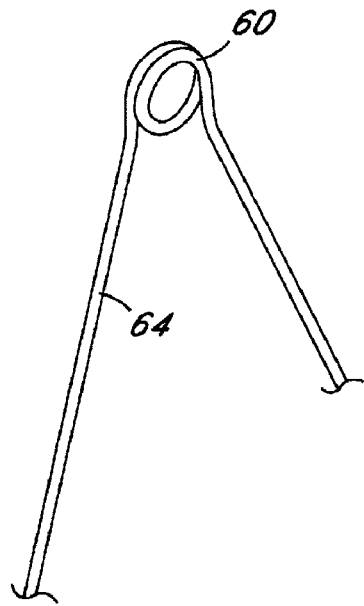
FIG. 17 is a fragmentary view of an apex in accordance with one aspect of the present invention.
Figure 18:
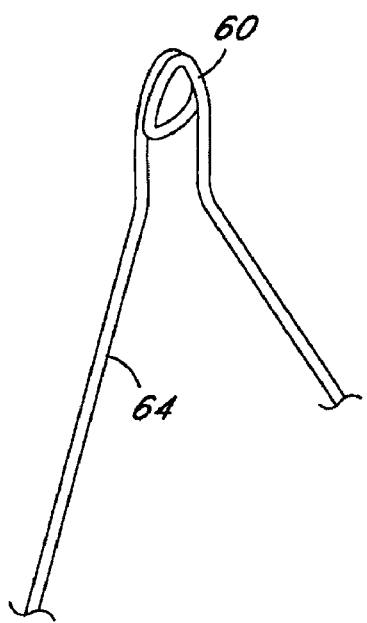
FIG. 18 is a fragmentary view of an alternate embodiment of an apex in accordance with the present invention.
Figure 19:
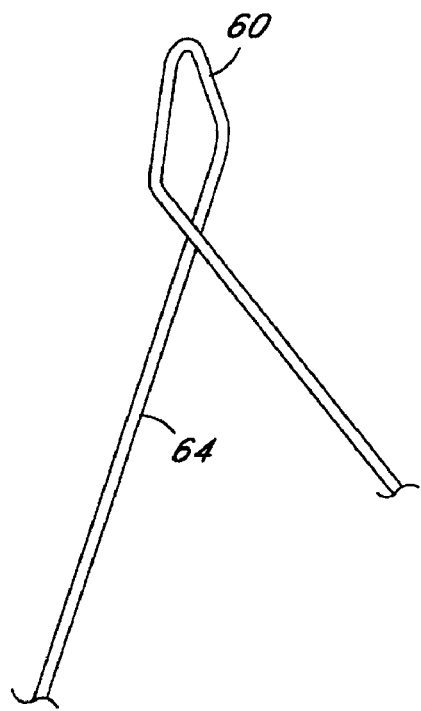
FIG. 19 is a further embodiment of an apex in accordance with the present invention.

FIGS. 15-22 illustrate alternative bend configurations in accordance with the present invention. FIG. 15 shows one embodiment having the proximal and distal bends as eyelets, but the connector bend 68, remaining in the usual configuration. The embodiment illustrated in FIG. 16 has the proximal and distal bends as well as the connector bend in the eyelet configuration. Various eyelet designs in accordance with the present invention are shown in greater detail in FIGS. 17-18, including a double-looped circular eyelet (FIG. 17), a double-looped triangular eyelet (FIG. 18), and a single-looped triangular eyelet (FIG. 19). The eyelets can be used to receive a circumferentially extending suture or wire as has been described.

Figure 20:
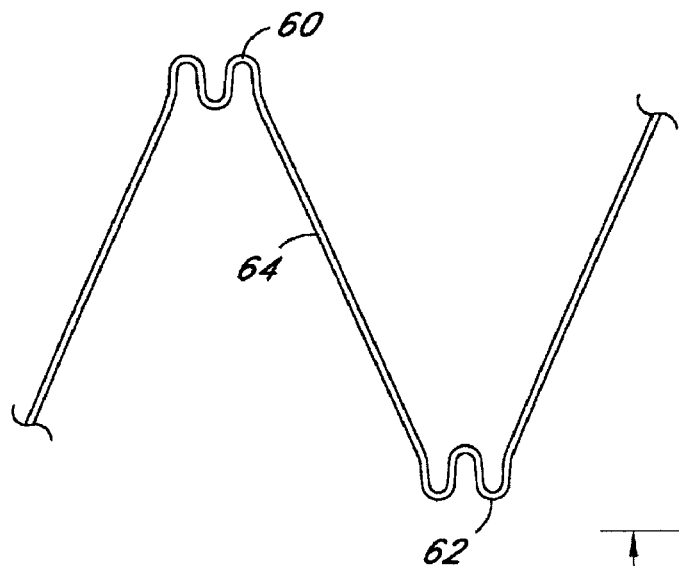
FIG. 20 is a fragmentary view of a further wire layout in accordance with the present invention.
Figure 21:
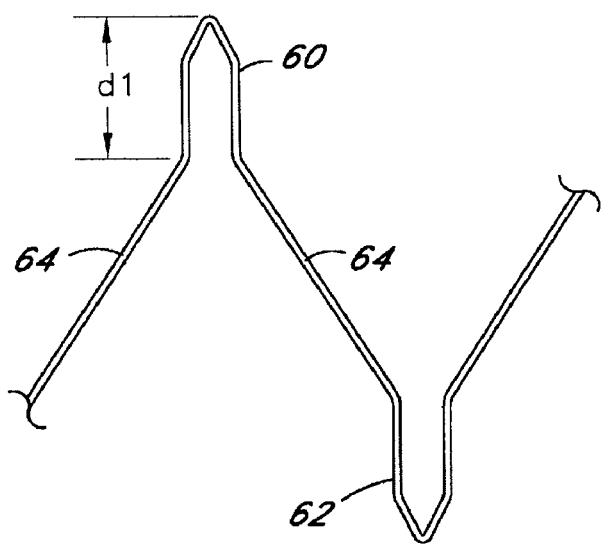
FIG. 21 is a fragmentary view of a further wire layout in accordance with the present invention.
Figure 22:
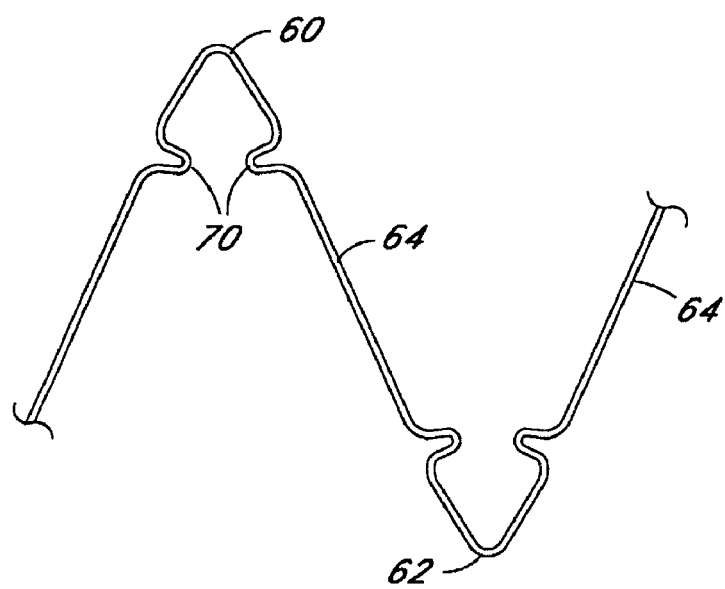
FIG. 22 is a fragmentary view of a further wire layout in accordance with the present invention.

Additional embodiments of the wire configuration are illustrated in FIGS. 20-22. FIG. 20 shows an embodiment of the proximal 60 and distal 62 bends in which double bends are employed to increase the flexion. Alternatively, FIG. 21 shows triangular bends having a more pronounced length (d1) of parallel wire, and accordingly shorter wall sections 64. Another embodiment of the proximal and distal bends is shown in FIG. 122, wherein the triangular bends include additional flexion points in the form of wall segment bends 70.

The elongate flexible tubular body 122 comprises an outer sheath 128 which is axially movably positioned upon an intermediate tube 130. A central tubular core 132 is axially movably positioned within the intermediate tube 130. In one embodiment, the outer tubular sheath comprises extruded PTFE, having an outside diameter of about 0.250" and an inside diameter of about 0.230". The tubular sheath 128 is provided at its proximal end with a manifold 134, having a hemostatic valve 136 thereon and access ports such as for the infusion of drugs or contrast media as will be understood by those of skill in the art.

The outer tubular sheath 128 has an axial length within the range of from about 40" to about 55", and, in one embodiment of the deployment device 120 having an overall length of 110 cm, the axial length of the outer tubular sheath 128 is about 52 cm and the outside diameter is no more than about 0.250". Thus, the distal end of the tubular sheath 128 is located at least about 16 cm proximally of the distal end 126 of the deployment catheter 120 in stent loaded configuration.

As can be seen from FIGS. 7 and 8, proximal retraction of the outer sheath 128 with respect to the intermediate tube 130 will expose the compressed iliac branches of the graft, as will be discussed in more detail below.

A distal segment of the deployment catheter 120 comprises an outer tubular housing 138, which terminates distally in an elongate flexible tapered distal tip 140. The distal housing 138 and tip 140 are axially immovably connected to the central core 132 at a connection 142.

The distal tip 140 preferably tapers from an outside diameter of about 0.225" at its proximal end to an outside diameter of about 0.070" at the distal end thereof. The overall length of the distal tip 140 in one embodiment of the deployment catheter 120 is about 3". However, the length and rate of taper of the distal tip 140 can be varied depending upon the desired trackability and flexibility characteristics. The distal end of the housing 138 is secured to the proximal end of the distal tip 140 such as by heat shrinking, thermal bonding, adhesive bonding, and/or any of a variety of other securing techniques known in the art. The proximal end of distal tip 140 is preferably also directly or indirectly connected to the central core 132 such as by a friction fit and/or adhesive bonding.

In at least the distal section of the catheter, the central core 132 preferably comprises a length of hypodermic needle tubing. The hypodermic needle tubing may extend throughout the length catheter to the proximal end thereof, or may be secured to the distal end of a proximal extrusion as illustrated for example in FIG. 8. A central guidewire lumen 144 extends throughout the length of the tubular central core 132, having a distal exit port 146 and a proximal access port 148 as will be understood by those of skill in the art.

Referring to FIGS. 7 and 8, a bifurcated endoluminal graft 150 is illustrated in a compressed configuration within the deployment catheter 120. The graft 150 comprises a distal aortic section 152, a proximal ipsalateral iliac portion 154, and a proximal contralateral iliac portion 156. The aortic trunk portion 152 of the graft 150 is contained within the tubular housing 138. Distal axial advancement of the central tubular core 132 will cause the distal tip 140 and housing 138 to advance distally with respect to the graft 150, thereby permitting the aortic trunk portion 152 of the graft 150 to expand to its larger, unconstrained diameter. Distal travel of the graft 150 is prevented by a distal stop 158 which is axially immovably connected to the intermediate tube 130. Distal stop 158 may comprise any of a variety of structures, such as an annular flange or component which is adhered to, bonded to or intregally formed with a tubular extension 160 of the intermediate tube 132. Tubular extension 160 is axially movably positioned over the hypotube central core 132.

The tubular extension 160 extends axially throughout the length of the graft 150. At the proximal end of the graft 150, a step 159 axially immovably connects the tubular extension 160 to the intermediate tube 130. In addition, the step 159 provides a proximal stop surface to prevent proximal travel of the graft 150 on the catheter 120. The function of step 159 can be accomplished through any of a variety of structures as will be apparent to those of skill in the art in view of the disclosure herein. For example, the step 159 may comprise an annular ring or spacer which receives the tubular extension 160 at a central aperture therethrough, and fits within the distal end of the intermediate tube 130. Alternatively, the intermediate tube 130 can be reduced in diameter through a generally conical section or shoulder to the diameter of tubular extension 160.

Proximal retraction of the outer sheath 128 will release the iliac branches 154 and 156 of the graft 150. The iliac branches 154 and 156 will remain compressed, within a first (ipsalateral) tubular sheath 162 and a second (contralateral) tubular sheath 164. The first tubular sheath 162 is configured to restrain the ipsalateral branch of the graft 150 in the constrained configuration, for implantation at the treatment site. The first tubular sheath 162 is adapted to be axially proximally removed from the iliac branch, thereby permitting the branch to expand to its implanted configuration. In one embodiment, the first tubular sheath 162 comprises a thin walled PTFE extrusion having an outside diameter of about 0.215" and an axial length of about 7.5 cm. A proximal end of the tubular sheath 162 is necked down such as by heat shrinking to secure the first tubular sheath 162 to the tubular extension 160. In this manner, proximal withdrawal of the intermediate tube 130 will in turn proximally advance the first tubular sheath 162 relative to the graft 150, thereby deploying the self expandable iliac branch of the graft 150.

The second tubular sheath 164 is secured to the contralateral guidewire 166, which extends outside of the tubular body 122 at a point 168, such as may be conveniently provided at the junction between the outer tubular sheath 128 and the distal housing 138. The second tubular sheath 164 is adapted to restrain the contralateral branch of the graft 150 in the reduced profile. In one embodiment of the invention, the second tubular sheath 164 has an outside diameter of about 0.215" and an axial length of about 7.5 cm. The second tubular sheath 164 can have a significantly smaller cross section than the first tubular sheath 162, due to the presence of the tubular core 132 and intermediate tube 130 within the first iliac branch 154.

The second tubular sheath 164 is secured at its proximal end to a distal end of the contralateral guidewire 166. This may be accomplished through any of a variety of securing techniques, such as heat shrinking, adhesives, mechanical interfit and the like. In one embodiment, the guidewire is provided with a knot or other diameter enlarging structure to provide an interference fit with the proximal end of the second tubular sheath 156, and the proximal end of the second tubular sheath 156 is heat shrunk and/or bonded in the area of the knot to provide a secure connection. Any of a variety of other techniques for providing a secure connection between the contralateral guidewire 166 and tubular sheath 156 can readily be used in the context of the present invention as will be apparent to those of skill in the art in view of the disclosure herein. The contralateral guidewire 166 can comprise any of a variety of structures, including polymeric monofilament materials, braided or woven materials, metal ribbon or wire, or conventional guidewires as are well known in the art.

In use, the free end of the contralateral guidewire 166 is percutaneously inserted into the arterial system, such as at a first puncture in a femoral artery. The contralateral guidewire is advanced through the corresponding iliac towards the aorta, and crossed over into the contralateral iliac in accordance with cross over techniques which are well known in the art. The contralateral guidewire is then advanced distally down the contralateral iliac where it exits the body at a second percutaneous puncture site.

Figure 9:
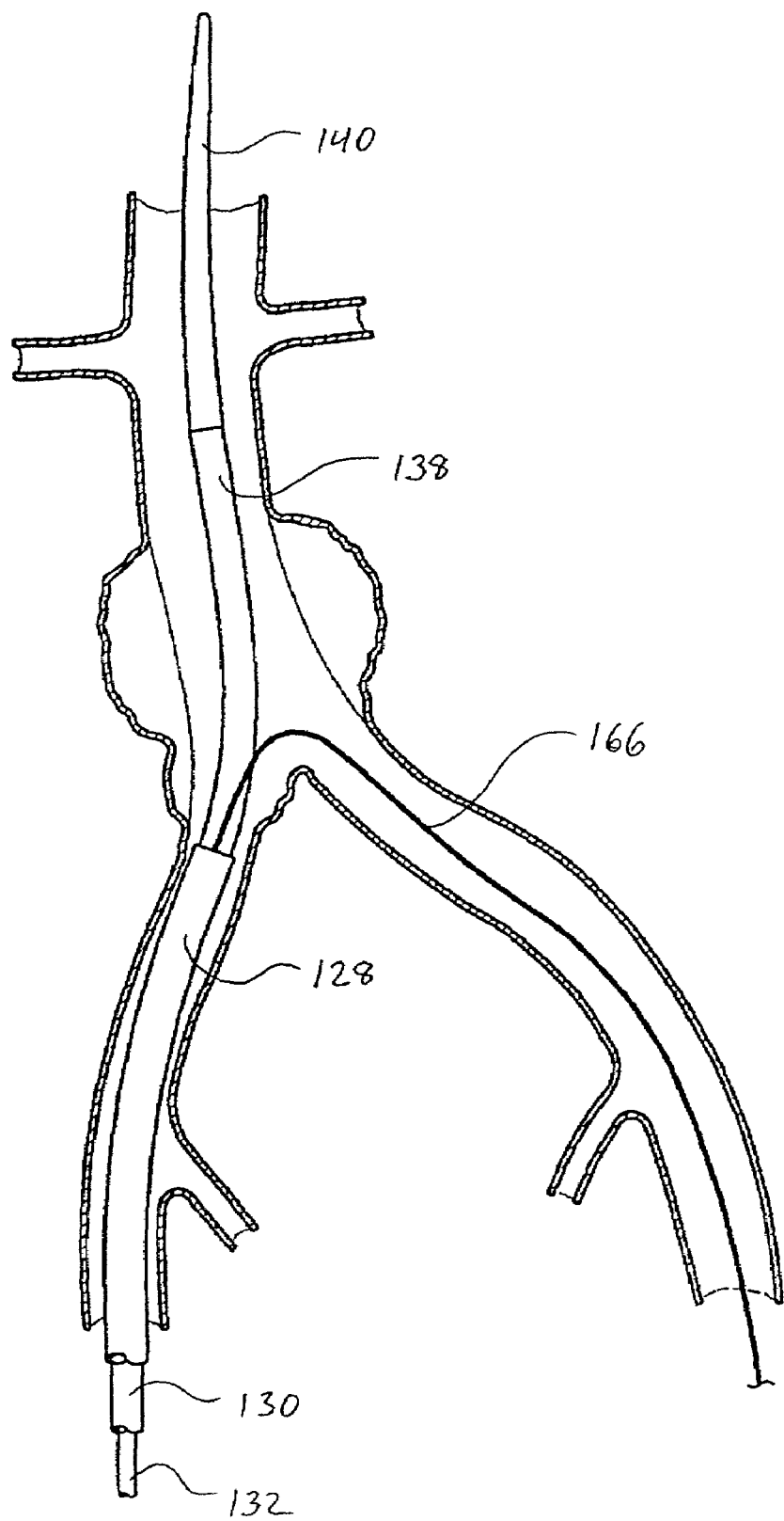
FIG. 9 is a schematic representation of the deployment catheter of the present invention positioned within the ipsalateral iliac and the aorta, with the contralateral guidewire positioned within the contralateral iliac.

The deployment catheter 120 is thereafter percutaneously inserted into the first puncture, and advanced along a guidewire (e.g. 0.035 inch) through the ipsalateral iliac and into the aorta. As the deployment catheter 120 is transluminally advanced, slack produced in the contralateral guidewire 166 is taken up by proximally withdrawing the guidewire 166 from the second percutaneous access site. In this manner, the deployment catheter 120 is positioned in the manner generally illustrated in FIG. 9.

Figure 10:
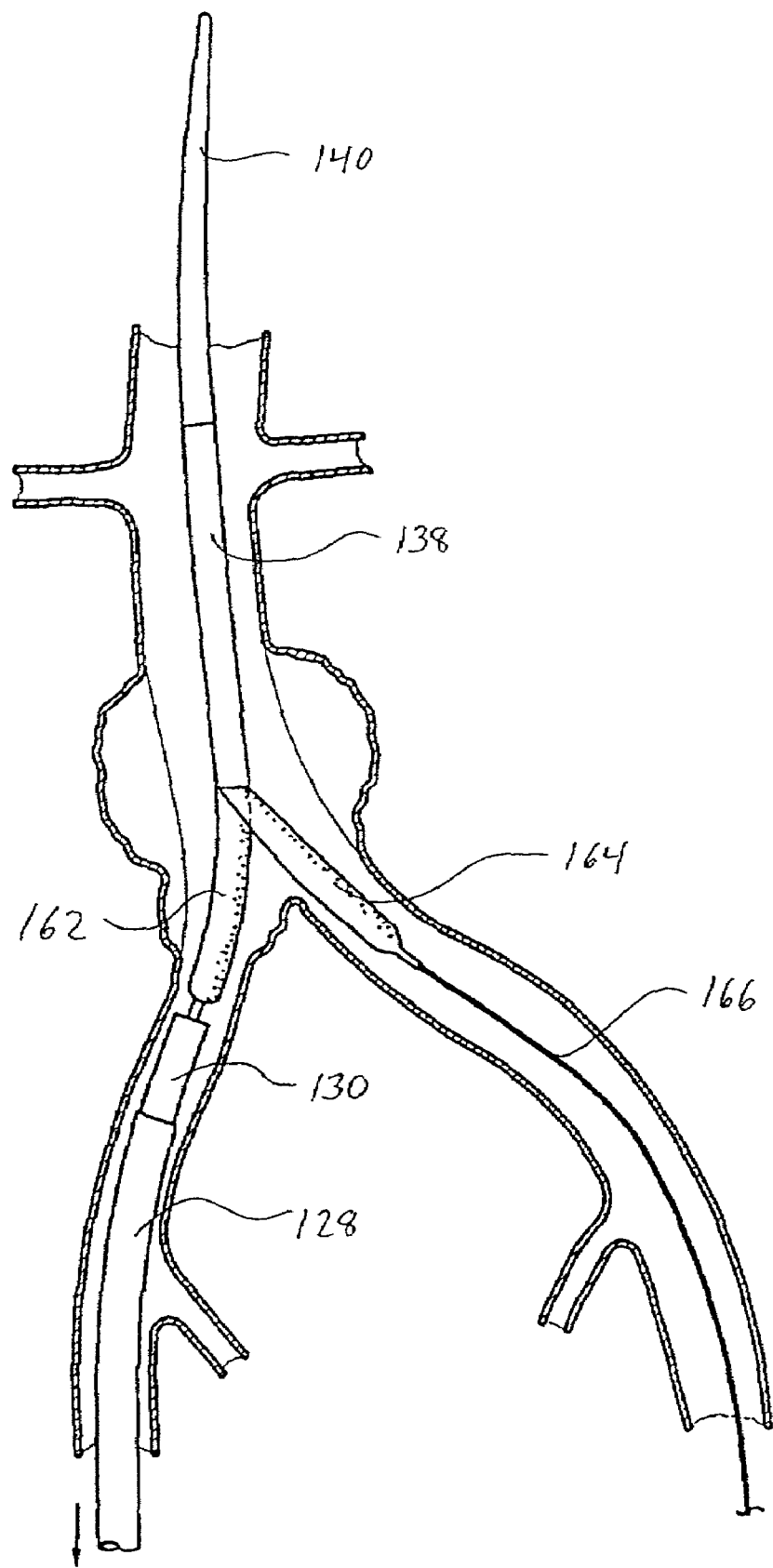
FIG. 10 is a schematic representation as in FIG. 9, with the outer sheath proximally retracted and the compressed iliac branches of the graft moving into position within the iliac arteries.

Referring to FIG. 10, the outer sheath 128 is proximally withdrawn while maintaining the axial position of the overall deployment catheter 120, thereby releasing the first and second iliac branches of the graft 150. Proximal advancement of the deployment catheter 120 and contralateral guidewire 166 can then be accomplished, to position the iliac branches of the graft 150 within the iliac arteries as illustrated.

Figure 11:
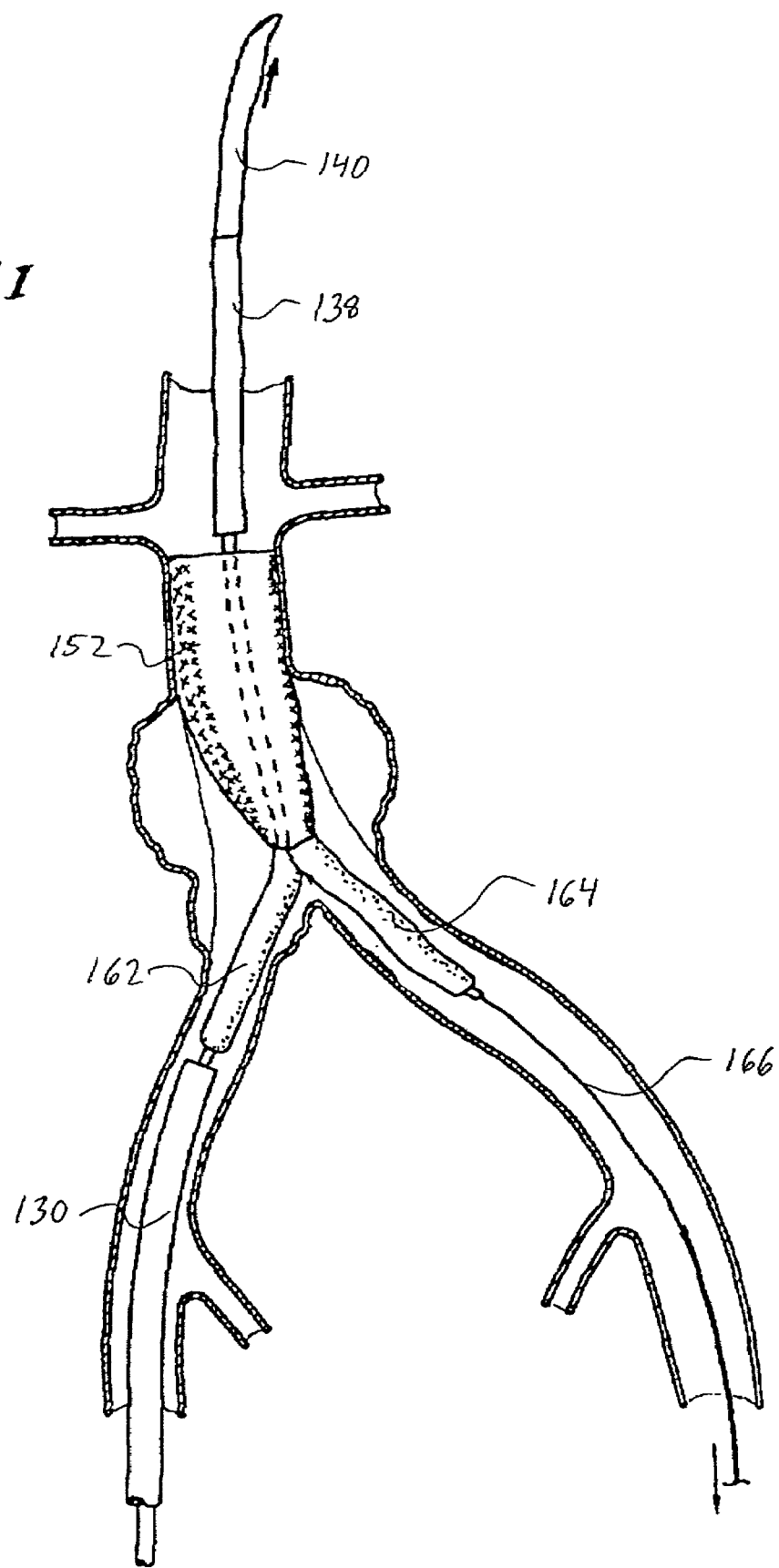
FIG. 11 is a schematic representation as in FIG. 10, with the compressed iliac branches of the graft within the iliac arteries, and the main aortic trunk of the graft deployed within the aorta.
Figure 12:
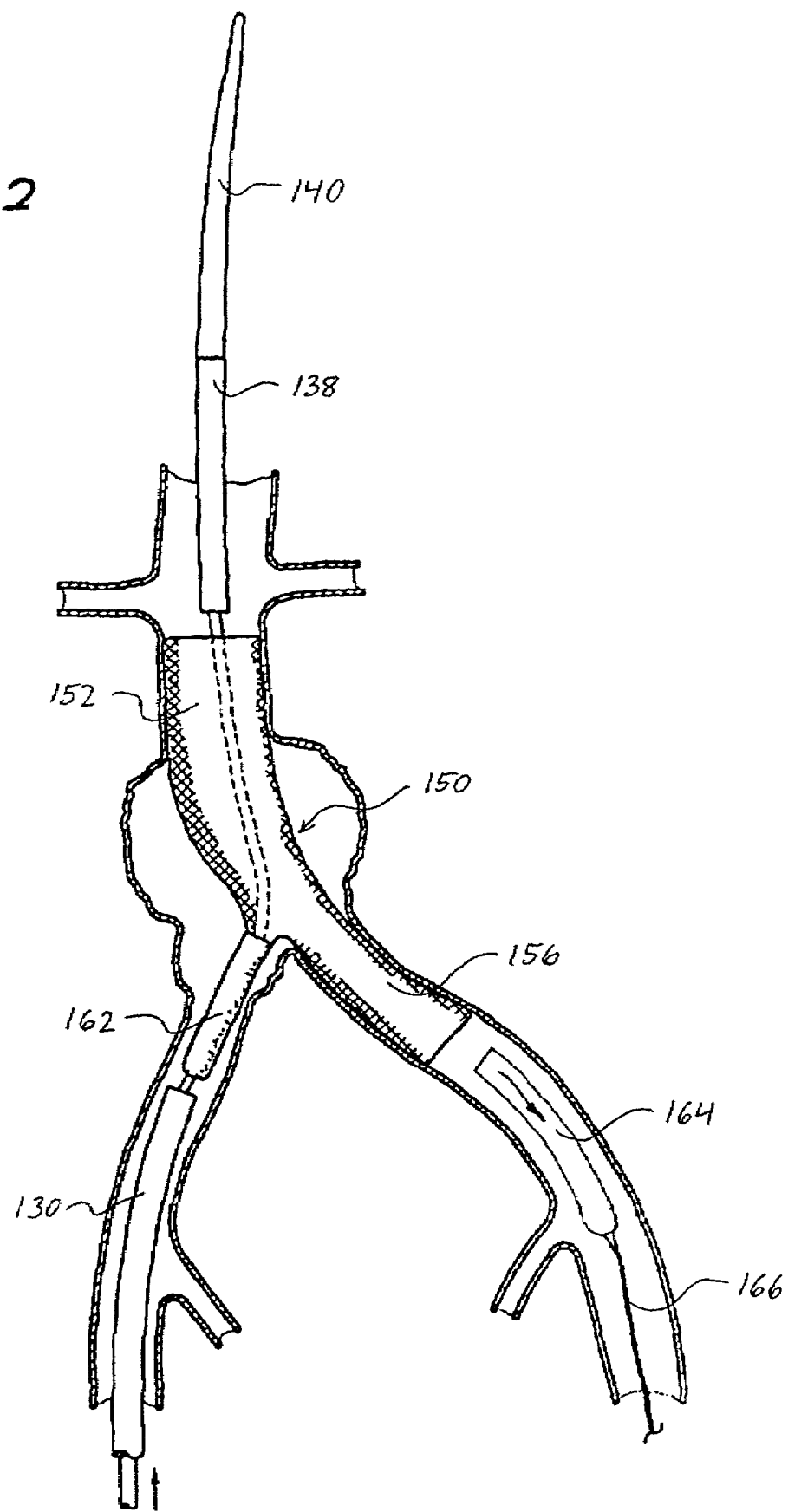
FIG. 12 is a schematic representation as in FIG. 11, with the contralateral iliac branch of the graft deployed.
Figure 13:
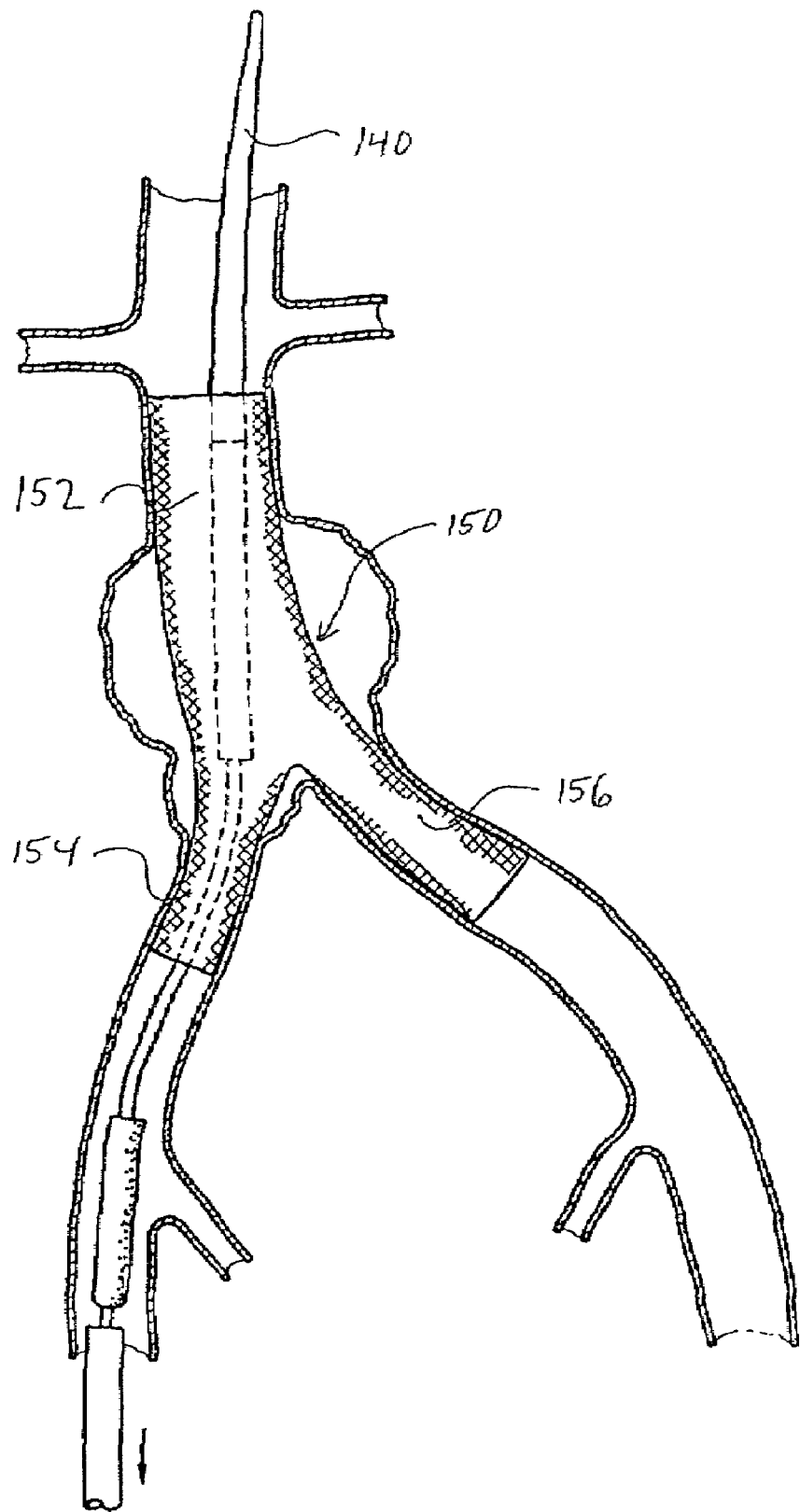
FIG. 13 is a schematic illustration as in FIG. 12, following deployment of the ipsalateral branch of the graft.

Referring to FIG. 11, the central core 132 is distally advanced thereby distally advancing the distal housing 138 as has been discussed. This exposes the aortic trunk of the graft 150, which deploys into its fully expanded configuration within the aorta. As illustrated in FIG. 12, the contralateral guidewire 166 is thereafter proximally withdrawn, thereby by proximally withdrawing the second sheath 164 from the contralateral iliac branch 156 of the graft 150. The contralateral branch 156 of the graft 150 thereafter self expands to fit within the iliac artery. The guidewire 166 and sheath 164 may thereafter be proximally withdrawn and removed from the patient, by way of the second percutaneous access site.

Thereafter, the deployment catheter 120 may be proximally withdrawn to release the ipsalateral branch 154 of the graft 150 from the first tubular sheath 162. Following deployment of the ipsalateral branch 154 of the prosthesis 150, a central lumen through the aortic trunk 152 and ipsalateral branch 154 is sufficiently large to permit proximal retraction of the deployment catheter 120 through the deployed bifurcated graft 150. The deployment catheter 120 may thereafter be proximally withdrawn from the patient by way of the first percutaneous access site.

While the foregoing embodiments of the present invention have been set forth in detail for the purposes of making a complete disclosure of the invention, the above-described embodiments of the invention are intended to be illustrative only. Numerous alternative embodiments may be devised by those skilled in the art without departing from the spirit and scope of the following claims.

What is claimed is:

1. A self-expandable bifurcated endoluminal prosthesis, comprising:
   a proximal wire support section having a proximal end, a distal end and a central lumen extending therethrough;
   a first wire branch section at the distal end of the proximal support; and
   a second wire branch section at the distal end of the proximal support;
   wherein at least the proximal wire support section and the first wire branch section are formed from a single length of wire and the wire in the proximal wire support section comprises a series of proximal bends and a series of distal bends, creating a series of struts connecting the proximal bends and distal bends to form at least two axially adjacent tubular segments, joined by a connector therebetween and wherein the series of proximal bends, distal bends and struts form a series of triangles, each triangle being defined by one proximal bend and two distal bends or two proximal bends and one distal bend, further wherein at least one of the proximal bends is pivotably connected to at least one of the distal bends.

2. An endoluminal prosthesis as in claim 1, wherein the proximal support comprises at least three segments and two connectors.

3. An endoluminal prosthesis as in claim 1, wherein the wire in at least one of the first and second wire branch sections comprises a series of proximal bends and a series of distal bends, creating a series of struts connecting the proximal bends and distal bends to form a tubular segment wall.

4. An endoluminal prosthesis as in claim 3, wherein at least some of the struts in at least one of the proximal wire support section, the first wire branch section, and the second wire branch section are substantially linear.

5. An endoluminal prosthesis as in claim 3, wherein each segment comprises from about 4 proximal bends to about 12 proximal bends.

6. An endoluminal prosthesis as in claim 1, further comprising an eye on at least one of the proximal and distal bends in at least one of the proximal wire support section, the first wire branch section, and the second wire branch section.

7. An endoluminal prosthesis as in claim 5, wherein the at least two axially adjacent tubular segments in the proximal wire support section comprises a first tubular segment and a second tubular segment that is axially adjacent to the first tubular segment and at least one eye on a distal end of the first tubular segment that is connected to at least one corresponding eye on a proximal end of the second tubular segment.

8. An endoluminal prosthesis as in claim 6, wherein the corresponding eyes are connected with a suture.

9. An endoluminal prosthesis as in claim 6, further comprising a polymeric layer on the wire support.

10. An endoluminal prosthesis as in claim 9, wherein at least some of the coffesponding eyes are connected with a metal link.

11. An endoluminal prosthesis as in claim 9, wherein at least a first distal bend in a first of the axially adjacent tubular segments is connected to at least a first proximal bend in a second of the axially adjacent tubular segments and at least one of the first proximal bend and the first distal bend comprise an eye.

12. An endoluminal prosthesis as in claim 1, further comprising a polymeric layer on the wire support.

13. An endoluminal prosthesis as in claim 9, wherein the layer comprises a tubular PTFE sleeve surrounding at least a central portion of the prosthesis.

14. An endoluminal prosthesis as in claim 1, wherein at least one of the first wire branch section and the second wire branch section comprises a series of proximal bends and a series of distal bends creating a series of struts connecting the proximal bends and distal bends to form at least a first tubular segment and a second tubular segment that is axially adjacent to the first tubular segment, and at least one eye on a distal end of the first tubular segment that is connected to at least one corresponding eye on a proximal end of the second tubular segment.

15. An endoluminal prosthesis as in claim 1, wherein at least a first distal bend in a first of the axially adjacent tubular segments is connected to at least a first proximal bend in a second of the axially adjacent tubular segments and at least one of the first proximal bend and the first distal bend comprise an eye.

16. A one piece endoluminal prosthesis, comprising an elongate flexible wire, formed into a plurality of axially adjacent tubular segments spaced along an axis and defining a central lumen therethrough, each tubular segment comprising a zig zag section of the wire having a plurality of proximal bends and distal bends that form a series of triangles that extend circumferentially around an axis of the graft, with the wire continuing between each adjacent tubular segment, wherein the prosthesis is radially compressible into a first, reduced cross sectional configuration for implantation into a body lumen, and self expandable to a second, enlarged cross sectional configuration at a treatment site in a body lumen, said prosthesis further comprising a first branch support section and a second branch support section each in communication with the lumen and each configured to extend into the branched arteries and at least one moveable link connecting at least one proximal bend to at least one distal bend.

17. An endoluminal prosthesis as in claim 16, further comprising an outer tubular sleeve surrounding at least a portion of the prosthesis.

18. An endoluminal prosthesis as in claim 16, wherein the plurality of axially adjacent tubular segments comprises a first tubular segment and a second tubular segment that is axially adjacent to the first tubular segment and at least one distal bend on the first tubular segment is connected to at least one proximal bend from the second tubular segment.

19. An endoluminal prosthesis as in claim 18, wherein the connection comprises a pivotable connection.

20. An endoluminal prosthesis as in claim 19, wherein the connection comprises a metal link.

21. An endoluminal prosthesis as in claim 16, wherein at least a portion of the prosthesis has an expansion ratio of at least about 1:4.

22. An endoluminal prosthesis as in claim 21, wherein at least a portion of the prosthesis has an expansion ratio of at least about 1:5.

23. An endoluminal prosthesis as in claim 16, wherein at least a portion of the prosthesis has an expanded diameter of at least about 20 mm -30 mm in an unconstrained expansion, and the prosthesis is implantable using a catheter no greater than about 16 French.

24. A prosthesis as in claim 23, wherein at least a portion of the prosthesis has an expanded diameter of at least about 25 mm, and is implantable on a delivery device having a diameter of no more than about 16 French.

25. An endoluminal prosthesis as in claim 16, wherein the first and second branch support sections are bilaterally symmetrical.

26. An endoluminal prosthesis as in claim 16, wherein the first and second branch support sections have a length within the range of about 1 cm to about 5 cm.

27. An endoluminal prosthesis as in claim 16, wherein at least one of the first branch support section and the second branch support section comprises a series of proximal bends and a series of distal bends creating a series of struts connecting the proximal bends and distal bends to form at least a first tubular branch segment and a second tubular branch segment that is axially adjacent to the first tubular branch segment.

28. An endoluminal prosthesis as in claim 27, further comprising a polymeric layer on the axially adjacent tubular segments.

29. An endoluminal prosthesis as in claim 28, further comprising an eye on at least some of the distal and proximal bends on at least one of the first branch support section and the second branch support section.

30. An endoluminal prosthesis as in claim 29, wherein at least a first distal bend in the first tubular branch segment is connected to at least a first proximal bend in the second tubular branch segment and at least one of the first proximal bend and the first distal bend comprise an eye.

31. An endoluminal prosthesis as in claim 16, further comprising an eye on at least some of the bends.

32. An endoluminal prosthesis as in claim 16, wherein at least a first distal bend in a first of the axially adjacent tubular segments is connected to at least a first proximal bend in a second of the axially adjacent tubular segments and at least one of the first proximal bend and the first distal bend comprise an eye.

* * * * *